United States Patent [19]

Johnson

[11] Patent Number: 4,490,538

[45] Date of Patent: Dec. 25, 1984

[54] ENLARGED-HETERO-RING PROSTACYCLIN ANALOGS

[75] Inventor: Roy A. Johnson, Kalamazoo, Mich.

[73] Assignee: The Upjohn Company, Kalamazoo, Mich.

[21] Appl. No.: 25,314

[22] Filed: Mar. 26, 1979

Related U.S. Application Data

[63] Continuation-in-part of Ser. No. 904,781, May 11, 1978, abandoned, which is a continuation-in-part of Ser. No. 788,143, Apr. 19, 1977, abandoned.

[51] Int. Cl.³ .................. C07D 311/94; C07D 407/06; A61K 31/35; A61K 31/41

[52] U.S. Cl. .................... 548/252; 548/253; 549/396; 424/269; 424/283

[58] Field of Search ............... 260/345.2 P; 549/396; 548/252, 253

[56] References Cited

U.S. PATENT DOCUMENTS 4,123,441 10/1978 Johnson .......................... 260/345.2

Primary Examiner—Robert Gerstl

Attorney, Agent, or Firm—Lawrence T. Welch; Morris L. Nielsen

[57] ABSTRACT

Processes for preparing dihydro-prostacyclin analogs, which are 9-deoxy-5,9-cyclic ethers of prostaglandin $F_1\alpha$-type compounds, illustrated, for example, by a compound of the formula

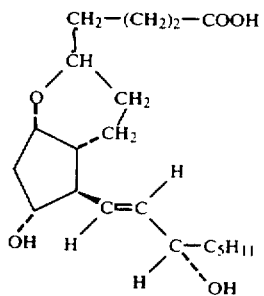

wherein $\sim$ indicates alpha or beta configuration; including the products and intermediates produced therein, said products having pharmacological utility.

76 Claims, No Drawings

ENLARGED-HETERO-RING PROSTACYCLIN ANALOGS

CROSS REFERENCE TO RELATED APPLICATIONS

This application is a continuation-in-part of copending application Ser. No. 904,781, filed May 11, 1978, which was a continuation-in-part of then copending application Ser. No. 788,143, filed Apr. 19, 1977, since abandoned.

BACKGROUND OF THE INVENTION

This invention relates to products having prostacyclin-like structure and to processes for preparing them. In particular this invention relates to prostacyclin-type compounds or analogs in which the 5-membered heterocyclic ring of prostacyclin is enlarged to 6-members with an additional methylene group, and in which the bond between the side chain and the heterocyclic ring is a saturated bond instead of a double bond.

Prostacyclin is an organic compound related to prostaglandins and identified as 9-deoxy-6,9α-epoxy-$\Delta^5$-PGF$_{1\alpha}$. It is particularly characterized as an enol ether from its chemical properties. See R. A. Johnson et al., Prostaglandins 12, 915 (1976).

The prostaglandins and analogs are well-known organic compounds derived from prostanoic acid which has the following structure and atom numbering:

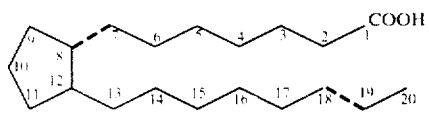

As drawn hereinafter the formulas represent a particular optically active isomer having the same absolute configuration as PGF$_{1\alpha}$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

Somewhat related compounds have been reported by C. Pace-Asciak et al., in Biochemistry, Vol. 10, pages 3657-3664 (1971), including, for example:

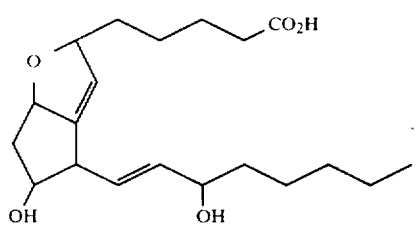

Prostacyclin and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undersirable gastrointestinal effects from systemic administration of prostaglandin synthetase inhibitors.

Because of these biological responses, prostacyclin and prostacyclin-type compounds are useful to study, prevent, control, or alleviate a wide variety of diseases and undesirable physiological conditions in mammals, including humans, useful domestic animals, pets, and zoological specimens, and in laboratory animals, for example mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of while blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001-1.0 μg./ml. of whole blood. These compounds are also useful in preparing platelet-rich concentrates from blood for use in treating thrombocytopenia or in chemotherapy.

Prostacyclin and prostacyclin-type compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostacyclin and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Prostacyclin and prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin or prostacyclin-type compound and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostacyclin and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, antiinflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostacyclin or prostacyclin-type compound is administered along with the anti-inflammatory prostaglandin synthetase inhibitor either by the same route of administration or by a different route. For example, if the anti-inflammatory substance is being administered orally, the prostacyclin or prostacyclin-type compound is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostacyclin or prostacyclin-type compound is also administered rectally. Further, the prostacyclin derivative can be conveniently administered orally or, in the case of women, vaginally. It is especially convenient when the administration route is to be the same for both anti-inflammatory substance and prostacyclin or prostacyclin-type compound to combine both into a single dosage form.

The dosage regimen for the prostacyclin or prostacyclin-type compound in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostacyclin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostacyclin or prostacyclin-type compound to reduce and then substantially to eliminate those undesirable effects.

Prostacyclin or prostacyclin-type compounds are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for neubulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostacyclin or prostacyclin-type compound can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

Prostacyclin or prostacyclin-type compounds are effectively administered to human asthma patients by oral inhalation or by aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as eethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

Prostacyclin or prostacyclin-type compounds are useful in mammals, including man, as nasal decongestants and are used for this purpose in a dose range of about 10 μg. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, nonobstructive mesenteric ischemia, arteritis lymphangitis and the like. These examples are included to be illustrative and should not be construed as limiting the term peripheral vasuclar disease. For these conditions the prostacyclin compounds are administered orally or parenterally via injection or infusion directly into a vein or artery, intra-venous or intra-arterial injections being preferred. The dosages of these compounds are in the range of 0.01–1.0 μg. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No. 74/0149 referenced as Derwent Farmdoc No. 58,400V. See Elliott, et al., Lancet, Jan. 18, 1975, pp. 140–142.

Prostacyclin or prostacyclin-type compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostacyclin or prostacyclin-type compounds are further useful for controlling the reproductive cycle in menstruating female mammals, including humans. By the term menstruating female mammals is meant animals which are mature enough to menstruate, but not so old that regular menstruation has ceased. For that purpose the prostacyclin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostacyclin or prostacyclin-type compounds are further useful in causing cervical dilation in pregnant and non-pregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostacyclin compounds is also useful in operative gynecology such as D and C (Cervical Dilation and Uterine Curettage) where mechanical dilation may cause performation of the uterus, cervical tears, or infections. It is also useful for diagnostic procedures where dilation is necessary for tissue examination. For these purposes, the prostacyclin compound is administered locally or systemically.

The prostacyclin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostacyclin and prostacyclin-type compounds are further useful in domestic animals as in abortifacients (especially for feedlot heifers), as an aid to estrus detection, and for regulation or synchronizatuon of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostacyclin compound is injected or applied in a feed at doses of 0.1–100 mg. per animal and may be combined with other agents such as steroids. Dosing schedules will depend on the species treated. For example, mares are given the prostacyclin compound 5 to 8 days after ovulation and return to estrus. Cattle are treated at regular intervals over a 3 week period to advantageouly bring all into estrus at the same time.

Prostacyclin or prostacyclin-type compounds increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or by intravenous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

These prostacyclin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared.

For those purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients; constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostacyclin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

SUMMARY OF THE INVENTION

It is the purpose of this invention to provide novel products having pharmacological activity. It is a further purpose to provide processes for preparing these products and their intermediates.

The presently provided cyclic ethers include compounds of the following formula:

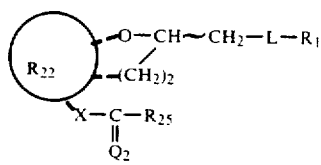

III wherein the terms L, $Q_2$, $R_1$, $R_{22}$, $R_{25}$, X, and ~ are as defined herein in the TABLE OF DEFINITION OF TERMS FOR FORMULAS.

TABLE

DEFINITION OF TERMS FOR FORMULAS

A is
 a valence bond or $-(CH_2)_h-$ wherein h is one, 2, or 3.

G is
 nitrato, iodo, chloro, bromo, acetato, trifluoroacetato or benzoato.

L is
 (1) a valence bond, (2) $-(CH_2)_d-$ wherein d is one to 5 inclusive, (3) $-(CH_2)_t-CF_2-$ wherein t is one, 2, or 3, (4) $-CH=CH-A-$ wherein A is a valence bond or $-(CH_2)_h-$ wherein h is one, 2, or 3, or (5) $-CH_2-O-CH_2-Y-$ wherein Y is a valence bond or $-(CH_2)_k-$ wherein k is one or 2.

Q is

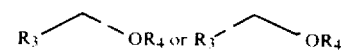

wherein $R_3$ is hydrogen or alkyl of one to 4 carbon atoms, inclusive, and wherein $R_4$ is hydrogen, tetrahydropyranyl, tetrahydrofuranyl, 1-ethoxyethyl or a group of the formula

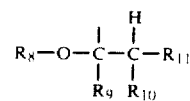

wherein $R_8$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_9$ and $R_{10}$ are the same or different, being hydrogen, alkyl of one to 4 carbon atoms, inclusive, phenyl or phenyl substituted with one, 2, or 3 alkyl of one to 4 carbon atoms, inclusive, or, when $R_9$ and $R_{10}$ are taken together, $-(CH_2)_a-$ or $-(CH_2)_b-O-(CH_2)_c-$ wherein a is 3, 4, or 5, b is one, 2, or 3, and c is one, 2, or 3 with the proviso that b plus c is 2, 3, or 4, and wherein $R_{11}$ is hydrogen or phenyl.

$Q_1$ is

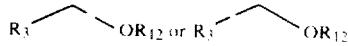

wherein $R_3$ is hydrogen or alkyl of one to 4 carbon atoms, inclusive, and wherein $R_{12}$ is the same as $R_{12}$ is the same as $R_4$ above except that it does not include hydrogen but includes only the blocking groups.

$Q_2$ is

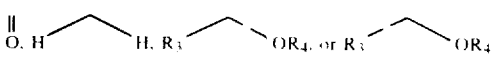

wherein $R_3$ and $R_4$ are as defined above for Q.

$Q_3$ is

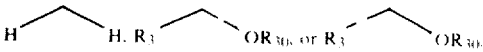

$Q_4$ is

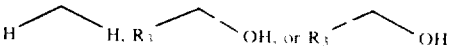

$R_1$ is (1) $-COOR_{19}$ (2) $-CH_2OH$ (3) $-CH_2N(R_{18})_2$ (4) $-\overset{O}{\underset{\|}{C}}-N(R_{18})_2$ (5) $-\overset{O}{\underset{\|}{C}}-NH-SO_2-R_{32}$ or

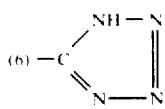

wherein R₁₉ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

(f) 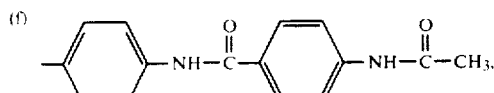

(g) 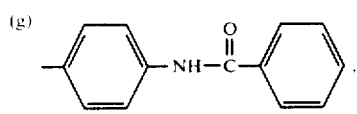

(h) 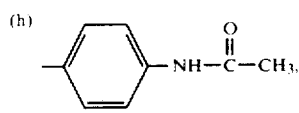

(i) 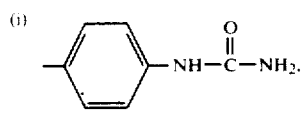

(j) 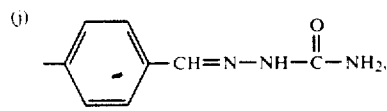

(k) 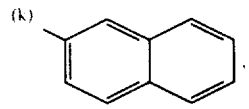

(l) 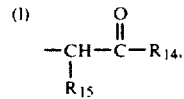

wherein R₁₄ is phenyl, p-bromophenyl, p-biphenylyl, p-nitrophenyl, p-benzamidophenyl, or 2-naphthyl, and wherein R₁₅ is hydrogen or benzoyl, (m) hydrogen, or (n) a pharmacologically acceptable cation; and wherein R₁₈ is hydrogen, alkyl of one to 12 carbon atoms, inclusive, benzyl, or phenyl, being the same or different, and wherein R₃₂ is hydrogen, alkyl of one to 12 carbon atoms, inclusive, aralkyl of 7 to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl in which the alkoxy group consists of one to 4 carbon atoms, inclusive.

R₂ is
hydrogen, alkyl of one to 12 carbon atoms, inclusive, or a pharmacologically acceptable cation.

R₃ is
hydrogen or alkyl of one to 4 carbon atoms, inclusive.

R₄ is
hydrogen, tetrahydropyranyl, tetrahydrofuranyl, 1-ethoxyethyl or a group of the formula

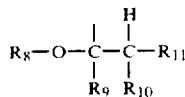

wherein R₈ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R₉ and R₁₀ are the same or different, being hydrogen, alkyl of one to 4 carbon atoms, inclusive, phenyl or phenyl substituted with one, 2, or 3 alkyl of one to 4 carbon atoms, inclusive, or, when R₉ and R₁₀ are taken together, —(CH₂)ₐ— or —(CH₂)ᵦ—O—(CH₂)ᶜ— wherein a is 3, 4, or 5, b is one, 2, or 3, and c is one, 2, or 3 with the proviso that b plus c is 2, 3, or 4, and wherein R₁₁ is hydrogen or phenyl.

R₅ and R₆ are
hydrogen, alkyl of one to 4 carbon atoms, inclusive, or fluoro, being the same or different, with the proviso that one of R₅ and R₆ is fluoro only when the other is hydrogen or fluoro.

R₇ is
alkyl of one to 4 carbon atoms, inclusive.

R₈ is
alkyl of one to 18 carbon atoms, inclusive cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive.

R₉ and R₁₀ are
the same or different, being hydrogen, alkyl of one to 4 carbon atoms, inclusive, phenyl or phenyl substituted with one, 2, or 3 alkyl of one to 4 carbon atoms, inclusive, or, when R₉ and R₁₀ are taken together, —(CH₂)ₐ— or —(CH₂)ᵦ—O—(CH₂)ᶜ— wherein a is 3, 4, or 5, b is one, 2, or 3, and c is one, 2, or 3 with the proviso that b plus c is 2, 3, or 4.

R₁₁ is
hydrogen or phenyl.

R₁₂ is
a blocking group respresented by tetrahydropyranyl, tetrahydrofuranyl, or a group of the formula

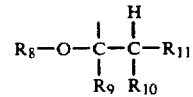

wherein R₈, R₉, R₁₀ and R₁₁ are as defined above.

R₁₃ is
the group

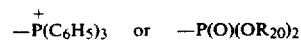

wherein R₂₀ is hydrogen or alkyl of one to 8 carbon atoms, inclusive.

R₁₄ is
phenyl, p-bromophenyl, p-biphenylyl, p-nitrophenyl, p-benzamidophenyl, or 2-naphthyl.

R₁₅ is
hydrogen or benzoyl.

R₁₆ is (1) —COOR₁₇

(2) —CH₂OH (3) —CH₂N(R₁₈)₂

(4) —C(=O)—N(R₁₈)₂ or

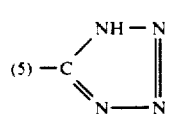

(5) —C wherein R₁₇ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl with one, 2, or 3 chloro or alkyl of one to 4 carbon atoms, inclusive, or (g) 2-naphthyl; wherein R₁₈ is hydrogen, alkyl of one to 12 carbon atoms, inclusive, benzyl, or phenyl, being the same or different.

R₁₇ and R₁₈ are
as defined above in R₁₆.

R₁₉ is
(a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive, (f) 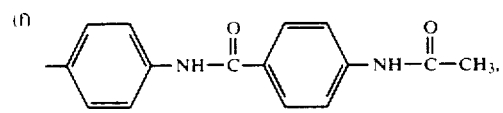

(g) 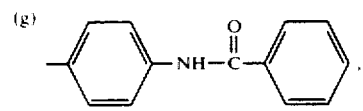

(h) 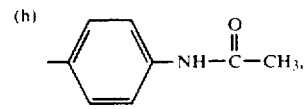

(i) 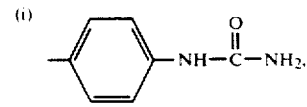

(j) 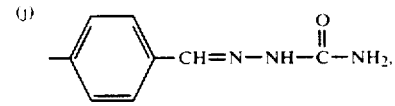

(k) 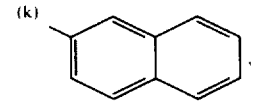

(l) 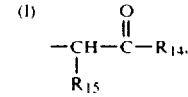

wherein R₁₄ R₁₅ are as defined above, (m) hydrogen or (n) a pharmacologically acceptable cation.

R₂₀ is
hydrogen or alkyl of one to 8 carbon atoms, inclusive.

(R₂₁) is

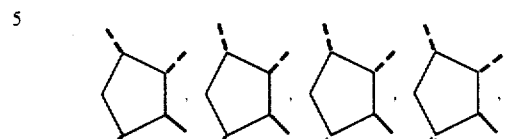

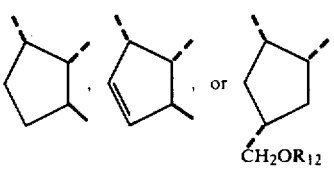

wherein R₁₂ is a blocking group as defined above.

(R₂₂) is

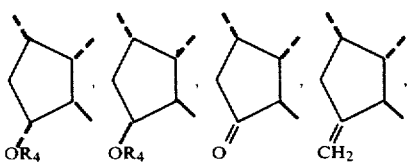

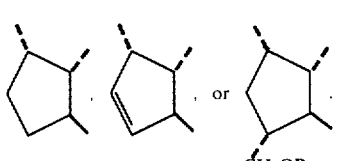

wherein R₄ is as defined above, i.e. hydrogen or a blocking group.

R₂₃ is
iodo or bromo.

R₂₄ is
alkyl of one to 4 carbon atoms, inclusive.

R₂₅ is (1) 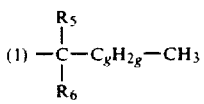
—C(R₅)(R₆)—C_gH_{2g}—CH₃ wherein $C_gH_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro;

(2) 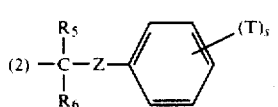

wherein R₅ and R₆ are as defined above with the proviso that neither R₅ nor R₆ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive between —CR$_5$R$_6$— and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2, or 3, with the proviso that not more than two T's are other than alkyl and when s is 2 or 3 the T's are either the same or different; or (3) 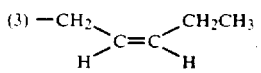

R$_{26}$ is (1) —COOR$_{19}$ (2) —CH$_2$OH (3) —CH$_2$N(R$_{18}$)$_2$ (4) 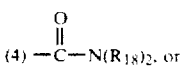

(5) 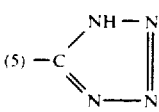

wherein R$_{19}$ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

(f) 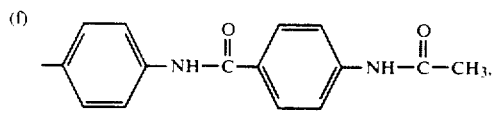

(g) 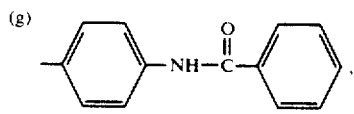

(h) 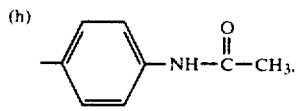

(i) 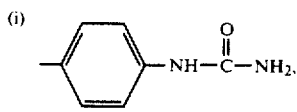

(j) 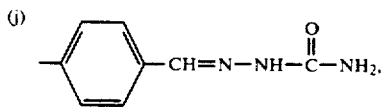

(k) 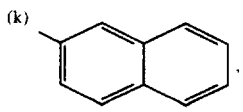

(1) hydrogen or (m) a pharmacologically acceptable cation, and wherein R$_{18}$ is hydrogen, alkyl of one to 12 carbon atoms, inclusive, benzyl, or phenyl, being the same or different.

R$_{27}$ is (a) alkyl of one to 12 carbon atoms, inclusive, (b) cycloalkyl of 3 to 10 carbon atoms, inclusive, (c) aralkyl of 7 to 12 carbon atoms, inclusive, (d) phenyl, (e) phenyl substituted with one, 2, or 3 chloro or alkyl of one to 4 carbon atoms, inclusive;

(f) 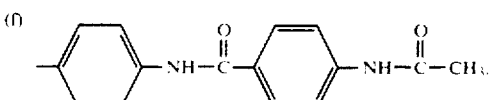

(g) 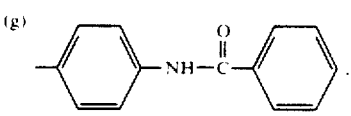

(h) 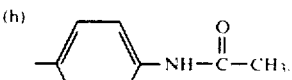

(i) 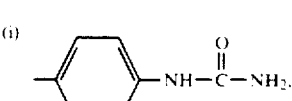

(j) 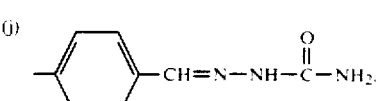

(k) 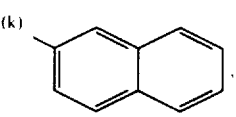

(1) hydrogen, or (m) a pharmacologically acceptable cation.

R$_{28}$ is

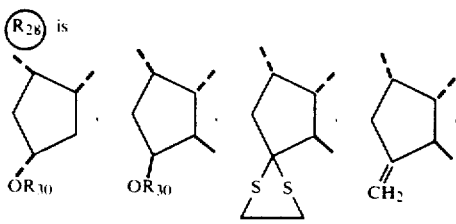

R$_{29}$ is

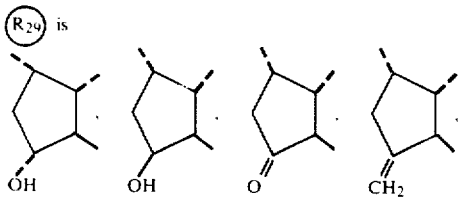

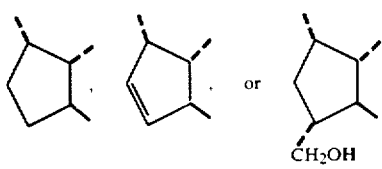 or

R30 is a blocking group represented by tetrahydropyranyl and the like defined by $R_{12}$, or a silyl group, $-Si(R_{31})_3$, wherein $R_{31}$ is alkyl of one to 4 carbon atoms, inclusive, phenyl, phenyl substituted with one or 2 fluoro, chloro, or alkyl of one of 4 carbon atoms, inclusive, or aralkyl of 7 to 12 carbon atoms, inclusive, the $R_{31}$ groups being the same or different.

$R_{31}$ is as defined immediately above.

$R_{32}$ is hydrogen, alkyl of one to 12 carbon atoms, inclusive, aralkyl of 7 to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl in which the alkoxy group consists of one to 4 carbon atoms, inclusive.

$R_{33}$ is

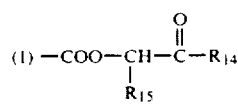

(2) $-CH_2OH$ (3) $-CH_2N(R_{18})_2$

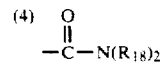

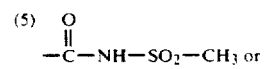

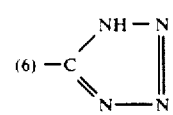

wherein $R_{14}$ is phenyl, p-bromophenyl, p-biphenylyl, p-nitrophenyl, p-benzamidophenyl, or 2-naphthyl, and wherein $R_{15}$ is hydrogen or benzoyl, wherein $R_{18}$ is hydrogen, alkyl of one to 12 carbon atoms, inclusive, benzyl, or phenyl, being the same or different.

$R_{34}$ is $-CH_2OH$ (1)

$-CH_2N(R_{18})_2$ (2)

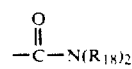 (3)

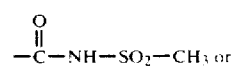 (4)

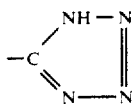 (5)

wherein $R_{14}$ is phenyl, p-bromophenyl, p-biphenylyl, p-nitrophenyl, p-benzamidophenyl, or 2-naphthyl, and wherein $R_{15}$ is hydrogen or benzoyl, wherein $R_{18}$ is hydrogen, alkyl or one to 12 carbon atoms, inclusive, benzyl, or phenyl, being the same or different.

T is alkyl of one 4 carbon atoms, inclusive, fluoro, chloro, trifluoromethyl, or $-OR_7$—wherein $R_7$ is alkyl of one to 4 carbon atoms, inclusive, and s is zero, one, 2, or 3, with the proviso that not more than two T's are other than alkyl and when s is 2 to 3 the T's are either the same or different.

X is cis— or trans—$CH=CH-$, $-C\equiv C-$, or $-CH_2CH_2-$.

Y is a valence bond or $-(CH_2)_k-$ wherein K is one or 2.

Z is an oxa atom ($-O-$) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive between $-CR_5R_6-$ and the phenyl ring.

a is 3, 4, or 5.

b is one, 2, or 3.

c is one, 2, or 3 with the proviso that b plus c is 2, 3, or 4.

d is one to 5 inclusive.

h is one, 2, or 3.

k is one or 2.

s is zero, one, 2, or 3.

t is one, 2, or 3.

~ indicates attachment is alpha or beta configuration.

$C_gH_{2g}$ is alkylene of one to 9 carbon atoms, inclusive, with one to 5 carbon atoms, inclusive, in the chain between $-CR_5R_6-$ and terminal methyl.

$C_jH_{2j}$ is a valence bond or alkylene of one to 9 carbon atoms, inclusive, substituted with zero, one, or 2 fluoro, with one to 6 carbon atoms, inclusive between $-CR_5R_6-$ and the phenyl ring.

Hal is chloro, bromo, or iodo.

END OF TABLE

By way of illustration, formula III represents 9-deoxy-5ξ,9α-epoxy-2,3-dinor-15(S)-15-methyl-PGF$_1$, when L is a valence bond, $Q_2$ is

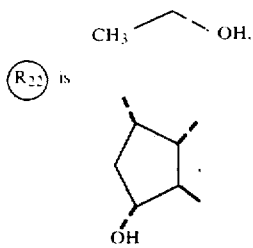

$R_{25}$ is n-pentyl, $R_1$ is —COOH, and X is trans—CH=CH—, and is compound represented by the formula:

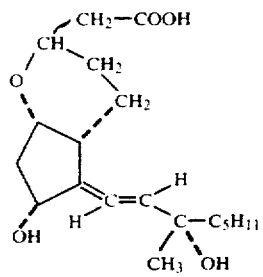

IV

Formula III represents 9-deoxy-5ξ,9α-epoxy-PGF$_1$, methyl ester, when L is ethylene, $Q_2$ is

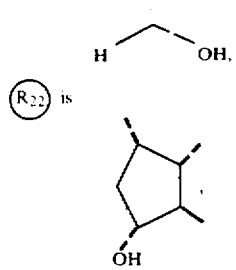

$R_{25}$ is n-pentyl, $R_1$ is —COOCH$_3$, and X is trans—CH=CH—, and is a compound represented by the formula

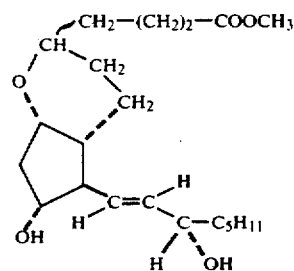

V

Included within the scope of $R_{22}$ in formula III, and following the above nomenclature, are 11β compounds, 11-deoxy-11-oxo (PGD) compounds, 11-deoxy-11-methylene compounds, 11-deoxy compounds, 11-deoxy-10,11-didehydro compounds, and 11-deoxy-11-hydroxymethyl compounds.

Considering the scope of $R_1$ in formula III, there are included acids, esters, salts, 2-decarboxy-2-hydroxymethyl compounds, 2-decarboxy-2-aminomethyl compounds, amides, and 2-decarboxy-2-tetrazolyl compounds.

The carbon atoms in the formulae herein are numbered as for prostanoic acid (I), except that the carbon atoms in longer or shorter side chains are named, following the usual convention, as "nor" or "homo" atoms. Thus in compound IV above, the —CH=CH— group is at the "13,14" position and, in the upper side chain, C-2 and C-3 are "nor" atoms. See N. A. Nelson, J. Medicinal Chem, 17, 911 (1974). Attachment to the $R_{22}$ ring is always at C-8, C-9 and C-12.

For those compounds of formula III wherein $Q_2$ is

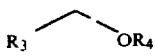

i.e. wherein the C-15 hydroxyl or ether group is attached to the side chain in alpha configuration, the configuration at C-15 is identical to that of the naturally occurring prostaglandins such as PGE$_1$ obtained from mammalian tissues. The 15-epimer compounds are represented by formula III when $Q_2$ is

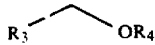

and are identified variously as "15-epi", or "15β" by the appropriate prefix in the name. As is known in the art, "15R" and "15S" designations depend on the neighboring substituents. See R. S. Cahn, J. Chem. Ed. 41, 116 (1964).

Included within these formula-III compounds are the isomers wherein ~ is in alpha or beta configuration. The nomenclature for these isomers may refer to "α" or "β" substitution at C-5 or, preferably, it may follow the "R" and "S" usage, for which see R. S. Cahn, and N. A. Nelson, both cited above. Assignment of the "R" and "S" configuration for the compounds herein is based on NMR spectral studies, both $^1$H and $^{13}$C, of model compounds. Differences between the names used herein and those applied in the predecessor application are due to the erroneous application therein of an empirical observation.

Following conventional usage, "5ξ" in a name refers to either "5R" or "5S" , whereas "(5RS)" refers to a mixture of 5R and 5S.

Although these formulas represent specific optical isomers, it is intended that the compounds are claimed not only in their purified form but also in mixtures, including racemic mixtures or mixtures of the enantiomeric forms.

With regard to formula III, examples of alkyl of one to 4 carbon atoms, inclusive, are methyl, ethyl, propyl, butyl, and isomeric forms thereof. Examples of alkyl of one to 8 carbon atoms, inclusive, are those given above and pentyl, hexyl, heptyl, octyl, and isomeric forms thereof. Examples of alkyl of one to 18 carbon atoms, inclusive, are those given and nonyl, decyl, undecyl, dodecyl, tridecyl, tetradecyl, pentadecyl, hexadecyl, heptadecyl, octadecyl, and isomeric forms thereof. Examples of cycloalkyl of 3 to 10 carbon atoms, inclusive, which includes alkyl-substituted cycloalkly, are
cyclopropyl,
2-methylcyclopropyl,
2,2-dimethylcyclopropyl,
2,3-diethylcyclopropyl,
2-butylcyclopropyl,
cyclobutyl, 2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.
Examples of aralkyl of 7 to 12 carbon atoms, inclusive, are
benzyl,
phenethyl,
1-phenylethyl,
2-phenylpropyl,
4-phenylbutyl,
3-phenylbutyl,
2-(1-naphthylethyl), and
1-(2-naphthylmethyl).
Examples of phenyl substituted by alkyl of one to 4 carbon atoms, inclusive, are
(o-, m-, or p-)tolyl,
p-ethylphenyl,
p-tert-butylphenyl, and
2,5-dimethylphenyl.

Examples of alkylene of one to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substituents on one or more carbon atoms thereof, e.g., —CH(CH$_3$)—, —C(CH$_3$)$_2$—, —CH(CH$_2$CH$_3$)—, —CH$_2$—CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH(CH$_3$)—. Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_gH_{2g}$ and hexamethylene, including hexamethylene with one or moe alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CHF—, —CF$_2$—CH$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CH$_2$—CF$_2$. Examples of

as defined above are phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl,
2-fluoro-(o-, m-, or p-)tolyl,
4-fluoro-2,5-xylyl,
(2,4-, 2,5-, 2,6-, 3,4-, or 3,5-)difluorophenyl, (o-, m-, or p-)chlorophenyl
2-chloro-p-tolyl,
(3-, 4-5-, or 6-)chloro-o-tolyl,
4-chloro-2-propylphenyl,
2-isopropyl-4-chlorophenyl,
4-chloro-3,5-xylyl,
(2,3-, 2,4-, 2,5-2,6-, 3,4-, or 3,5-)dichlorophenyl,
4-chloro-3-fluorophenyl,
(3, or 4)chloro-2-fluorophenyl,
α, α, α,-trifluoro-(o-, m-, or p-)tolyl,
(o-, m-, or p-)methoxyphenyl,
(o-, m-, or p-)ethoxyphenyl,
(4- or 5-)chloro-2-methoxyphenyl, and
2,4-dichloro(5- or 6-)methoxyphenyl.

Examples of phenyl substituted with one, 2, or 3 chloro are
(o-, m-, or p-)-chlorophenyl
2,4-dichlorophenyl and
2,4,6-trichlorophenyl.
Examples of phenyl substituted with hydroxycarbonyl or alkoxycarbonyl in which the alkoxy group consists of one to 4 carbon atoms, inclusive, are
(o-, m-, or p-)-carboxyphenyl
methyl (o-, m-, or p-)-carboxyphenyl
and
isopropyl (o-, m-, or p-)-carboxyphenyl.

Included in this invention are the pharmacologically acceptable salts when $R_{19}$ in —COOR$_{19}$ of $R_1$ is hydrogen. Pharmacologically acceptable salts of these formula-III compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The novel 4,5-dihydro-prostacyclin-type compounds of formula III have qualitatively the same pharmacological properties described above for prostacyclin or prostacyclin-type compounds and can be used for the same purposes and in the same manner described above. But, quite surprisingly, these novel 4,5-dihydro-prostacyclin-type compounds are substantially more specific with regard to potency in causing prostacyclin-like biological responses. Therefore each of these novel prostacyclin analogs is more useful than prostacyclin for at least one of the pharmacological purposes indicated above. Use of the novel analog for that purpose results in smaller undesired side effects than when prostacyclin is used for the same purpose. Moreover, because of its prolonged activity, fewer and smaller doses of the novel analog can frequently be used to attain the desired result.

These 4,5-dihydro-prostacyclin-type compounds are especially useful for inhibition of platelet aggregation in blood for either in vivo or in vitro applications described above.

Certain compounds within the scope of formula II are useful as hypotensive agents to reduce blood pressure in mammals, including man. These include the following:
(5R)-9-deoxy-5,9α-epoxy-PGF$_1$, methyl ester
(5R)-9-deoxy-5,9α-epoxy-PGF$_1$, amide
(2E,5S)-9-deoxy-5,9α-epoxy-2,3-didehydro-PGF$_1$, methyl ester
(2E,5S)-9-deoxy-5,9α-epoxy-2,3-didehydro-PGF$_1$
(2E,5R)-9-deoxy-5,9α-epoxy-2,3-didehydro-PGF$_1$, methyl ester
(2E,5R)-9-deoxy-5,9α-epoxy-2,3-didehydro-PGF$_1$
(5R)-9-deoxy-5,9α-epoxy-13,14-dihydro-PGF$_1$
(2E,5S)-9-deoxy-5,9α-epoxy-2,3-didehydro-13,14-dihydro-PGF$_1$, methyl ester
(2E,5S)-9-deoxy-5,9α-epoxy-2,3-didehydro-13,14-dihydro-PGF$_1$ For this purpose, the compounds are administered by intravenous infusion at the rate of about 0.01 to about 50 μg. per kg. of body weight per minute or in the single or multiple doses of about 25 to 500 μg. per kg. of body weight total per day.

To obtain the optimum combination of biological response specificity, potency, and duration of activity, certain compounds within the scope of the formulas III are preferred. For example it is preferred that $Q_2$ be

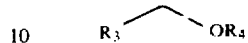

wherein it is especially preferred that $R_3$ be hydrogen or methyl, and that $R_4$ be hydrogen.

Another preference for the compounds of formula III is that $R_{19}$ in —COOR$_{19}$ be either hydrogen or alkyl of one to 12 carbon atoms, inclusive, especially one to 4, and more especially methyl or ethyl, for optimum absorption on administration, or a pharmacologically acceptable cation.

For oral administration it is preferred that $R_1$ in compounds of formula III be either

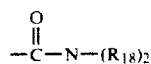

wherein $R_{18}$ is especially hydrogen or methyl, both $R_{18}$'s being the same or different, or

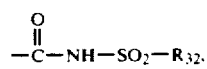

wherein $R_{32}$ is especially methyl.

When $R_{25}$ in the compounds of formula III is

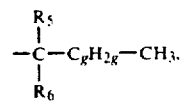

it is preferred that $C_gH_{2g}$ be alkylene of 2, 3, or 4 carbon atoms and especially that it be trimethylene. It is further preferred that $R_5$ and $R_6$ be hydrogen, methyl, ethyl, or fluoro, being the same or different. It is further preferred, when $R_5$ and $R_6$ are not hydrogen, that both $R_5$ and $R_6$ be methyl or fluoro. It is especially preferred that $R_{25}$ be n-pentyl, 1,1-dimethylpentyl, or 1,1-difluoropentyl.

When $R_{25}$ in the compounds of formula III is

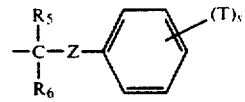

it is preferred that "s" be either zero or one. When "s" is not zero, it is preferred that T be methyl, chloro, fluoro, trifluoromethyl, or methoxy with meta or para attachment to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene. It is especially preferred that $R_{25}$ be

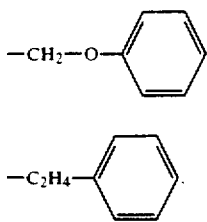

As to variations in (R$_{22}$) in the compounds of formulas III, it is preferred that (R$_{22}$) be

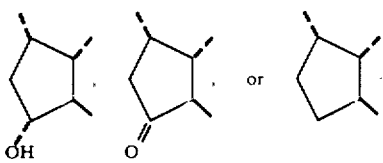

As to variations in L in compounds of formula III, it is preferred that L be —(CH$_2$)$_3$—, —(CH$_2$)$_4$, or —(CH$_2$)$_5$— and especially —(CH$_2$)$_3$—.

There are also provided mercury compounds of the formula

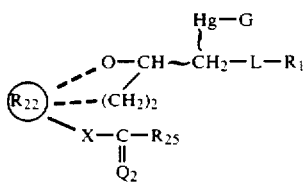

wherein G is nitrato, iodo, chloro, bromo, acetato, trifluoroacetato, or benzoato; and wherein L, Q$_2$, (R$_{22}$), R$_{25}$, R$_1$, X, and ~ are as defined above.

The novel mercury compounds disclosed herein are useful for pharmacological purposes. They have antiprotozoal and antisyphitlitic activity and are consequently effective in treating streptococci and staphylococci. They have antimicrobial activity and are useful for topical antiseptic treatment for animals, including humans, useful domestic animals, pets, zoological specimens, and laboratory animals. They are further useful in ophthalmiatrics.

For these purposes, these mecury compounds are preferably administered topically, for example in alcoholic solution at 0.002 to 0.01% concentration with a benzalkonium chloride as a preservative, or as a lotion, cream, or ointment in 0.5-5.0% concentration in combination with the usual pharmaceutically acceptable diluents. The exact application and concentration depends on such factors as the age, weight and condition of the subject.

Certain mercury compounds within the scope of formula XXXIV are preferred for optimum biological response specificity, potency, and duration of activity. For example it is preferred that Q$_2$ be

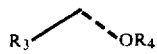

wherein R$_4$ is hydrogen; it is further preferred that L be trimethylene. When R$_3$ is alkyl, it is preferred that R$_3$ be methyl. Likewise, as to R$_1$, when R$_{19}$ in —COOR$_{19}$ is alkyl, it is preferred that R$_{19}$ be alkyl of one to 4 carbon atoms, especially methyl. Another preference in that G be chloro or acetato.

The cyclic ethers of formula III are produced by reactions and procedures described and exemplified hereinafter, as shown schematically in the charts.

Chart A will make clear the steps by which a cyclic ether of formula VIII is prepared by starting with a lactone of formula VIII, (a) reducing that lactone to a lactol of formula IX, (b) reacting that lactol with an anion derived from a substituted propionic acid or propionate of the formula

R$_{20}$OOC—CH$_2$CH$_2$—R$_{13}$

CHART A

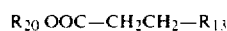

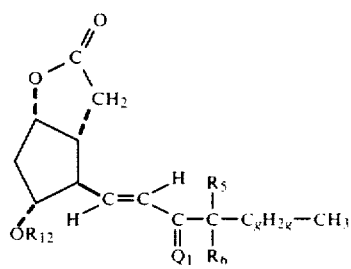

VIII (a)

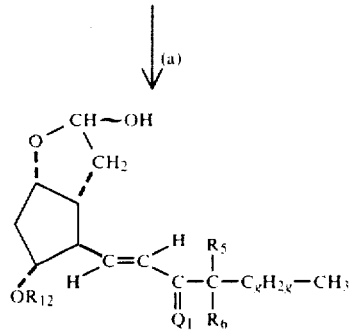

IX (b)

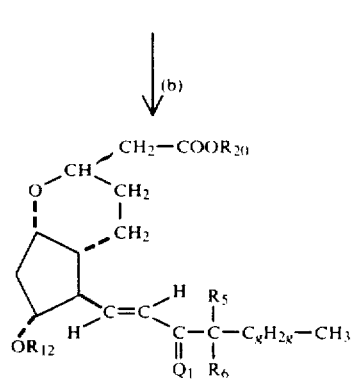

X (c)

-continued
CHART A

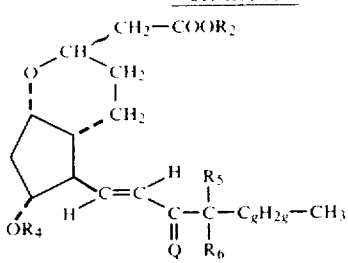
VII wherein $R_{20}$ is hydrogen or alkyl of one to 8 carbon atoms, inclusive, and $R_{13}$ is the group

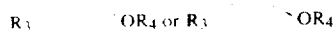

to produce a compound of formula X, and (c) transforming the product of step (b) to the formula-VII compound by methods known in the art, including optional acid hydrolysis of blocking groups $R_{12}$, saponification of ester groups $R_{20}$, and reesterification as desired within the scope of $R_2$.

In Chart A, the terms $C_gH_{2g}$, $R_4$, $R_5$, $R_6$, and $\sim$ have the same meaning as for compound III above. In addition, Q is

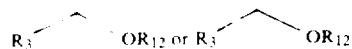

wherein $R_3$ is as defined for compound III, $Q_1$ is

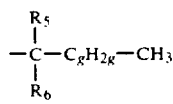

wherein $R_{12}$ is the same as $R_4$ defined above except that it does not include hydrogen but includes only the blocking groups such as tetrahydropyran-2-yl, $R_2$ is hydrogen, alkyl of one to 12 carbon atoms, inclusive, or a pharmacologically acceptable cation, and wherein $R_{20}$ is hydrogen or alkyl of one to 8 carbon atoms, inclusive.

The formula-VIII starting materials for Chart A are lactone intermediates known in the art or readily available by processes known in the art. For example, when $R_{12}$ is tetrahydropyran-2-yl ("THP") and $$-\overset{R_5}{\underset{R_6}{C}}-C_gH_{2g}-CH_3$$

in n-pentyl, see Corey et al., J. Am. Chem. Soc. 92,397 (1970). When $R_5$ and $R_6$ are methyl or ethyl, see U.S. Pat. No. 3,954,833. When $R_5$ and $R_6$ are fluoro, see U.S. Pat. No. 3,962,293. When Q is

see U.S. Pat. No. 3,864,387 and 3,931,279.

The formula-IX lactol is obtained in step (a) on reduction of lactone VIII without reducing the ethylenic group. For this purpose, diisobutylaluminum hydride is used as known in the art. The reduction is preferably done at $-60°$ to $-78°$ C.

The formula-X intermediate is obtained from the lactol in step (b) by reaction with an anion derived from either a phosphonopropionate of the formula

XI or a carboxyethylphosphonium compound of the formula

XII wherein $R_{20}$ is alkyl of one to 8 carbon atoms, inclusive, and Hal is chloro, bromo, or iodo. Alternatively, the phosphonium compound may be referred to by its ylid form,

XIIa

The reaction is done in the presence of a base, preferably potassium t-butoxide or sodium hydride for XI, or potassium t-butoxide, sodium ethoxide, benzyltrimethylammonium hydroxide, or preferably, an alkali metal hydroxide for XII, usually at 0°-25° C.

The formula-VII product is obtained in step (c) on replacement of the $R_{12}$ blocking groups with hydrogen, by acid hydrolysis, for example in dilute acetic acid, aqueous citric acid, or aqueous phosphoric acid-tetrahydrofuran. When $R_2$ in the product is different than $R_{20}$, transformation is brought about by methods known in the art, including saponification to yield the acid, optionally followed by esterification. Esters are conveniently prepared by interaction of the acid with an appropriate diazohydrocarbon. For example, when diazomethane is used, the methyl esters are produced. Similar use of diazoethane, diazobutane, and 1-diazo-2-ethylhexane for example, gives the ethyl, butyl, and 2-ethylhexyl esters, respectively. Of these esters, it is preferred that $R_2$ by methyl or ethyl.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389-394 (1954).

An alternative method for esterification of the acid compounds herein comprises transformations of the free acid to the corresponding silver salt, followed by interaction of that salt with an alkyl iodide. Examples of suitable iodides are methyl iodide, ethyl iodide, butyl iodide, and isobutyl iodide. The silver salts are prepared by conventional methods, for example, by dissolving the acid in cold dilute aqueous ammonia, evaporating the excess ammonia at reduced pressure, and then adding the stoichiometric amount of silver nitrate.

As for all of the reactions described herein, the duration of the reaction is readily determined by monitoring with TLC (thin layer chromatography).

Chart B shows the steps by which a cyclic ether of formula XIII is prepared by starting with a 4,5,-cis-didehydro-PGF$_{1\alpha}$ type compound of formula XIV, halogenating and cyclizing that formula-XIV compound to form a compound of formula XV, and subjecting the formula-XV compound to reductive dehalogenation.

In Chart B, the terms L, Q$_2$, 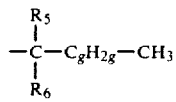, R$_{25}$, X and ~ are defined as for compound III above. In addition R$_{16}$ is
(1) —COOR$_{17}$
(2) —CH$_2$OH
(3) —CH$_2$N(R$_{18}$)$_2$

CHART B

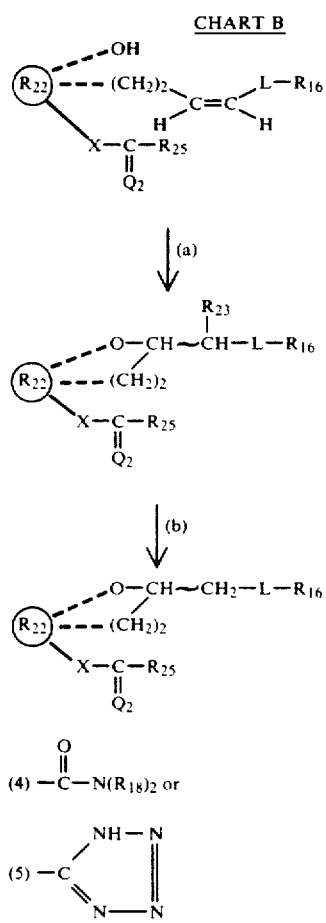

wherein R$_{17}$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl with one, 2, or 3 chloro or alkyl of one to 4 carbon atoms, inclusive, or (g) 2-naphthyl;

wherein R$_{18}$ is hydrogen, alkyl of one to 12 carbon atoms, inclusive, benzyl, or phenyl, being the same or different; and R$_{23}$ is iodo or bromo.

The starting materials of formula XIV are 4,5-cis-didehydro-PGF$_{1\alpha}$ type compounds (alternately "$\Delta^4$-PGF$_{2\alpha}$ type compounds") known in the art or readily available by processes known in the art. As to 4,5-cis-didehydro-PGF$_{1\alpha}$, 4,5-cis-didehydro-15(S) or (R)-15-methyl-PGF$_{1\alpha}$, 4,5-cis-17,18-cis-tetradehydro-PGF$_{1\alpha}$, and their methyl esters, see U.S. Pat. No. 3,954,835; as to 4,5-cis-didehydro-16,16-dimethyl-PGF$_{1\alpha}$ and other analogs within the scope of $$-\overset{R_5}{\underset{R_6}{C}}-C_gH_{2g}-CH_3$$

see U.S. Pat. No. 3,933,889; as to 2-decarboxy-2-aminomethyl-PGF$_1$ analogs, see U.S. Pat. No. 4,081,478, as to 16-phenoxy analogs, see Netherlands Pat. No. 7703950, Derwent Farmdoc Abstract No. 80703Y, as to 4,5-cis-didehydro-17-phenyl-18,19,20-trinor-PGF$_{1\alpha}$, see Belgian Pat. No. 842,275 or Derwent Farmdoc No. 92410X; as to 11-deoxy-11-oxo analogs, see Belgian Pat. No. 846,340; and as to 13,14-cis-CH=CH— analogs, see Belgian Pat. No. 844,105 or Derwent Farmdoc No. 05676Y.

As to a general method for preparing 4,5-cis-didehydro-PGF$_{1\alpha}$ analogs, see U.S. Pat. No. 3,933,889, particularly columns 21–23 and 36–50. Therein a lactol of formula

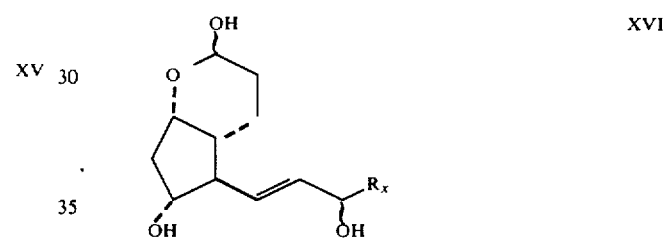

is transformed to a 4,5-cis-didehydro-PGF$_{1\alpha}$ type product by condensation with a Wittig reagent derived from a 3-carboxypropyltriphenylphosphonium halide and sodio methylsulfinylcarbanide.

Accordingly that method is useful for preparing 4,5-cis-didehydro-PGF$_{1\alpha}$ compounds within the scope of XIV as to R$_{25}$, including 16-phenoxy-17,18,19,20-tetranor compounds, by using formula-XVI lactols wherein R$_x$ is replaced by R$_{25}$.

Likewise that method is useful for preparing 4,5-cis-didehydro-PGF$_{1\alpha}$ compounds within the scope of XIV as to L by using an appropriate Wittig reagent. For example, 4,5-cis-didehydro-2-nor-PGF$_{1\alpha}$ is obtained by using (2-carboxyethyl)triphenylphosphonium bromide, and 4,5-cis-didehydro-2-homo-PGF$_{1\alpha}$ is obtained by using (4-carboxybutyl)triphenylphosphonium bromide.

2,2-difluoro-4,5-cis-didehydro-PGF$_{1\alpha}$ is obtained using a 3-carboxy-2,2-difluoro-propyltriphenylphosphonium halide. That phosphonium compound is available from the reaction of triphenylphosphine and 4-bromo-2,2-difluorobutanoic acid. This fluoro-acid and others within the scope of Br—CH$_2$—(CH$_2$)$_t$—CF$_2$—COOH     XXIV useful for preparing similar 2,2-difluoro-4,5-cis-didehydro-PGF$_{1\alpha}$ analogs are obtained by the steps of Chart C. In Chart C and in formula XXIV, "t" is 1,2, or 3; R$_{24}$ is alkyl of one to 4 carbon atoms, preferably methyl.

Other 4,5-cis-didehydro-PGF$_{1\alpha}$ and -13,14-dihydro-PGF$_{1\alpha}$ compounds within the scope of XIV wherein Q$_2$ is

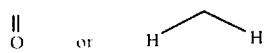

are available by methods disclosed herein or known in the art. For the 15-deoxy compounds, for example, the lactols are available by Wittig alkylation with phsophonamides of the formula

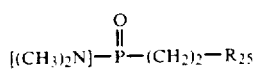

as disclosed in U.S. Pat. No. 4,112,224.

With reference to Chart C, the straight chain ω-bromo alkanoic acids of formula XVII are known in the art or may be prepared by methods known in the art. The formula-XVIII aldehyde is prepared from the formula-XVII acid by methods known in the art. For example, the formula-XVII acid may be reduced to its corresponding primary alcohol using lithium aluminum hydride, and the resulting alcohol then oxidized to form the formula-XVIII aldehyde by the Collins reagent (CrO$_3$-pyridine).

The formula-XIX cyanohydrin is then formed by methods known in the art, for example, using aqueous sodium cyanide, or by sulfite addition reaction. The formula-XX α-hydroxy alkanoic acid is then formed by methods known in the art, for example using hydrolysis under acidic conditions in dimethylsulfoxide solvent at reflux temperature. Thereafter the formula-XXI α-keto alkanoic acid is formed by oxidation of the formula-XX compound by methods known in the art. For this purpose the Jones reagent may be advantageously used.

The formula-XXII ester wherein R$_{24}$ is alkyl of one to 4 carbon atoms, preferably methyl, is then prepared from the formula-XXI acid by known methods described herein.

CHART C

Br—CH$_2$—(CH$_2$)$_t$—COOH     XVII

↓

Br—CH$_2$—(CH$_2$)$_t$—CHO     XVIII

↓

Br—CH$_2$—(CH$_2$)$_t$—C(OH)H—CN     XIX

↓

-continued
CHART C

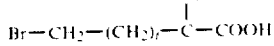     XX

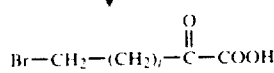     XXI

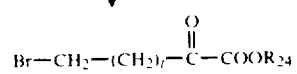     XXII

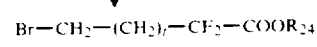     XXIII

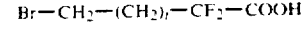     XXIV

The formula-XXIII ω-bromo alpha difluoro alkanoic acid ester is then prepared by fluorination, reacting molybdenum hexafluoride and boron trifluoride with the formula-XXII alpha keto alkanoic acid ester. This reaction is advantageously carried out in a methylene chloride solvent with reaction temperatures of below −35° C. Finally the formula-XXIV free acid is prepared by saponification of the formula-XXIII methyl ester.

Other 4,5-cis-didehydro-PGF$_{1\alpha}$ type starting materials within the scope of formula XIV are readily available by methods described above or known in the art. Generally they are prepared from lactols of the formula

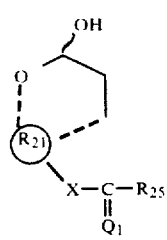     XXV wherein Q$_1$, (R$_{21}$), R$_{25}$, X, and ~ are as defined herein. These formula-XXV lactols are available from lactones of the formula

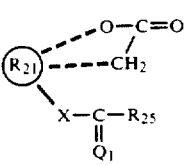     XXVI which are known in the art or readily available by methods known in the art.

When (R₂₁) is

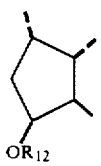

these 11β lactones are obtained by isomerizing a corresponding lactone having the 11α configuration, with suitable blocking at the C-15 position if desired, by methods known in the art, such as by way of the 11-mesylate or 11-tosylate. For application of the 11-benzoate for example, see Mitsunobu et al., J. Am. Chem. Soc. 94, 679 (1972).

When (R₂₁) is

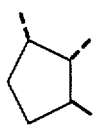

and R₂₅ is alkyl, see U.S. Pat. No. 3,931,279 and Derwent Farmdoc Abstract No. 10695V; when R₂₅ is phenyl-substituted, also see U.S. Pat. No. 3,931,279.

When (R₂₁) is

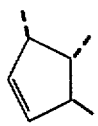

a suitable starting material is

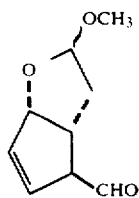

XXVII

See E. J. Corey et al., Tetrahedron Lett. 107 (1972). After introduction of the R₂₅-containing side chain by known methods including the Wittig reaction and reduction of the 15-oxo group, the methyl ether is hydrolyzed to the lactone in acid.

When (R₂₁) is

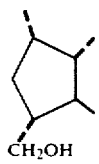

the lactone is available or prepared by processes known in the art. See Ger. Offen. 2,437,622 and Derwent Farmdoc Abstract No. 12714W. For example a compound of the formula

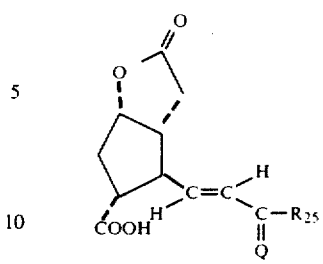

XXVIII is reduced at the —COOH position to the corresponding —CH₂OH compound using diborane.

In step "a" of Chart B, the starting material XIV is subjected to halogenation and cyclization to yield the formula-XV halo compounds. For related cyclization procedures see Staninets and Shilov, Chem. Abs. 64, 12625h (1966). For iodination there is used either an aqueous system containing iodine, potassium iodide, and an alkali carbonate or bicarbonate, or an organic solvent system such as dichloromethane containing iodine in the presence of an alkali metal carbonate. The reaction is carried out at temperatures below 25° C., preferably about 0°-5° C. for 10-20 hrs. Thereafter the reaction is quenched with sodium sulfite and sodium carbonate and the formula-XV compound separated from the reaction mixture. For bromination, N-bromosuccinimide or N-bromoacetamide is used. See Fieser et al., Reagents for Organic Synthesis, Vol. 1, pp. 74 and 78, Vol. IV p. 51.

In step "b" of Chart B the halo compound XV is subjected to reductive dehalogenation. Useful reagents include tributyltin hydride, triphenyltin hydride, sodium borohydride in ethanol or dimethyl sulfoxide, and zinc in acetic acid. Especially preferred is tributyltin hydride freshly prepared from tributyltin chloride and lithium aluminum hydride. The reaction is run in a solvent such as benzene at about 15°-35° C. and monitored by TLC.

Thereafter, any blocking groups are removed by methods known in the art and product XIII isolated by methods described herein or known in the art, for example by chromatography on silica gel.

A product within the scope of formula XIII may be transformed by methods known in the art or described herein to a product within the scope of formula III. Thus, if Q₂ in formula XIII is

it can be transformed to

by methods known in the art. See for example U.S. Pat. No. 3,728,382.

As another illustration, if R₁₀ is formula XIII is —COOCH₃, it can be transformed into any one of the substituted phenyl ester groups of —COOR₁₉ by first saponifying that methyl ester to yield the free acid and then reesterifying the acid to yield the substituted phenyl ester using methods known in the art. See for example U.S. Pat. No. 3,894,062.

Chart D shows a preferred route to the amides of formula XXXI and the amines of formula XXXII. The halo acid XXIX is transformed to the halo amide XXX which then yields the amide XXXI by reductive dehalogenation. On further reduction of the amide, the amine XXXII is obtained using wellknown methods. In Chart D, the terms L, $Q_2$, $(R_{22})$, $R_{25}$, $R_{23}$, X, and ~ are as defined above for Chart B, and $R_{18}$ is hydrogen, alkyl of one to 12 carbon atoms, inclusive, benzyl, or phenyl, being the same or different.

Another method of preparing the cyclic ethers within the scope of formula III is by reductive mercuration of a compound of formula VI shown in Chart E, wherein the terms G, L, $Q_2$, $(R_{22})$, $R_{25}$, $R_1$, X, and are as defined above.

Chart E shows the steps by which a 4,5-cis-didehydro-PGF$_{1\alpha}$-type compound of formula XXXIII is (a) converted to a mercury compound of formula VI and (b) compound VI is subjected to reductive demercuration to form the formula-III product.

Reference to Chart E will make clear the steps of this process. For background on this mercuration-demercuration cyclization see, for example, H. C. Brown et al., Organometal. Chem. Syn. 1, 7 (1970) and Fieser and Fieser, Reagents, N.Y., 1972.

The Formula-XXXIII starting materials have been discussed above for Chart B.

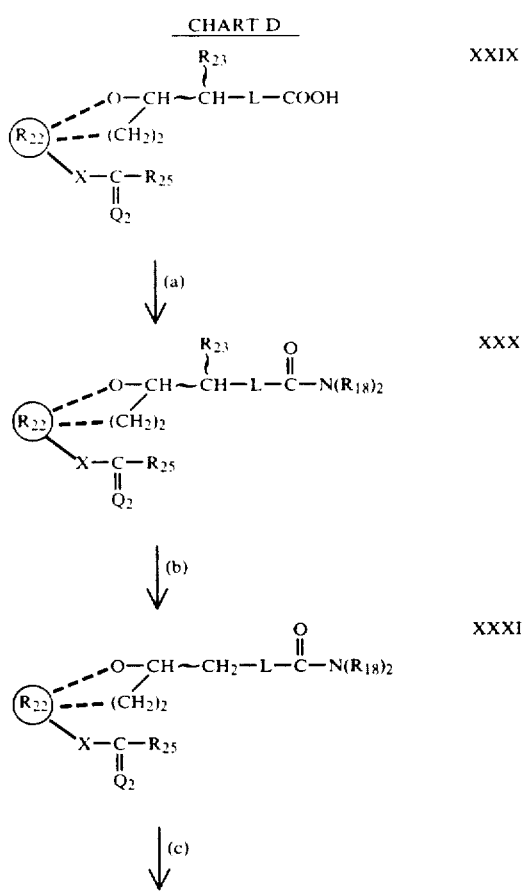

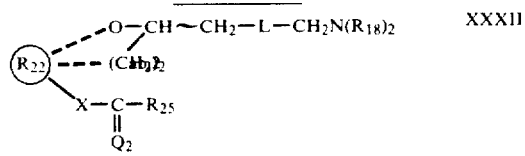

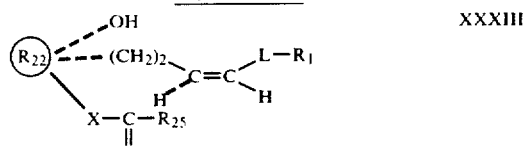

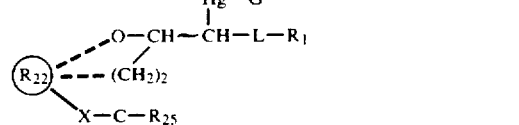

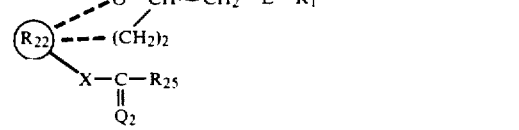

Additionally, as to substituted phenyl esters see U.S. Pat. No. 3,894,062, as to substituted phenacyl esters see U.S. Pat. No. 3,979,440, and as to 2-decarboxy-2-tetrazolyl derivatives see U.S. Pat. Nos. 3,883,513 and 3,932,389. In step "a" of Chart E, the starting material is reacted with an appropriate mercury (II) salt corresponding to Hg(G)$_2$, for example mercuric nitrate, chloride, or acetate. Preferred is either mercuric acetate or trifluoroacetate. The reagent is dissolved in either water or acid, e.g. acetic acid, and combined with a solution of the formula-XXXIII starting material in a solvent such as chloroform or tetrahydrofuran. The reaction is conveniently done at about 15°-35° C.

In step "b" of Chart E the mercurio compound is subjected to reductive demercuration. Useful reagents for this step include sodium borohydride, sodium amalgam, and hydrazine. Especially preferred is sodium borohydride.

The reaction is carried out in a solvent such as tetrahydrofuran at about 15°-35° C. Thereafter the mercury is separated, blocking groups removed if necessary, and the product isolated by methods described herein.

The formula-VI mercurio compounds are useful not only as intermediates for preparing the formula-III products but also for their pharmacological applications as set forth herein. G may be varied, for example, by suitable choice of reagent Hg(G)$_2$ or by replacement, for example of acetate by chloro by ion exchange.

Compounds of formula III wherein L is —CH=CH— are prepared by the process of Chart F. The starting materials of formula XXXV are available herein or by obvious transformations, for example from the formula-XIII compounds of Chart B. For background in preparing $\Delta^2$-prostaglandin analogs, see for example U.S. Pat. No. 4,024,174.

For those compounds of formula XIII in which

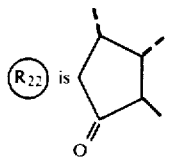 is it is preferred that the carbonyl groups be blocked, for example by thioketalization. For this purpose a reagent such as 1,2-ethanedithiol is employed in the presence of a Lewis acid, such as boron trifluoride etherate. The reaction is conveniently run at room temperature, and ordinarily proceeds to completion within several hours.

In Chart F, blocking groups $R_{30}$ in 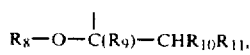 or $Q_3$ are either tetrahydropyranyl and the like as defined by $R_{12}$ above, or silyl groups, —Si(A)$_3$, as defined herein.

When the blocking group $R_{30}$ is tetrahydropyranyl or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess, preferably 1.0 to 1.2 times theory, and the reaction is carried out at about 20°-50° C.

When $R_{30}$ is of the formula $$R_8-O-C(R_9)-CHR_{10}R_{11},$$

as defined herein, including 1-ethoxyethyl, the appropriate reagent is a vinyl ether, e.g. ethyl vinyl ether, isopropenyl methyl ether, isobutyl vinyl ether, or any vinyl ether of the formula $R_8-O-C(R_9)=CR_{10}R_{11}$ wherein $R_8$, $R_9$, $R_{10}$, and $R_{11}$ are as defined above; or an unsaturated cyclic or heterocyclic compound, e.g. 1-cyclohex-1-yl methyl ether

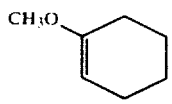

or 5,6-dihydro-4-methoxy-2H-pyran

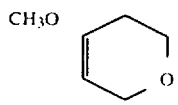

CHART F

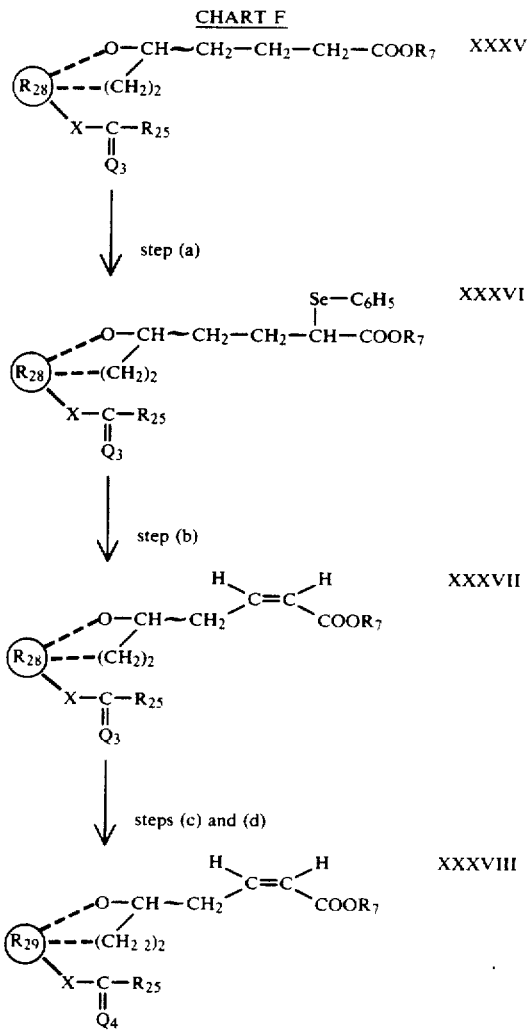

See C. B. Reese et al., J. Am. Chem. Soc. 89, 3366 (1967). The reaction conditions for such vinyl ethers and unsaturates are similar to those for dihydropyran above.

When the blocking group $R_{30}$ is silyl of the formula —Si(A)$_3$, the formula-XIII compound is transformed to a silyl derivative of formula XXXV by procedures known in the art. See, for example, Pierce, "Silylation of Organic Compounds," Pierce Chemical Co., Rockford, Ill. (1968). The necessary silylating agents for these transformations are known in the art or are prepared by methods known in the art. See, for example Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted mono-chlorosilanes suitable for this purpose include chlorotrimethylsilane, chlorotriisobutylsilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silylating agents suitable for forming the formula-XXXV intermediates include pentamethylsilylamine, pentaethylsilylamine, N-trimethylsilydiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

Referring to Chart F, in step (a) selenylation is achieved by first forming 2-lithium or 2-sodium derivatives of the formula-XXXV compounds, for example by reaction with a lithium or sodium amide formed from a secondary amine such as N-isopropylcyclohexylamine. Thereafter the formula-XXXVI compounds are obtained by reaction with diphenyl diselenide or benzeneselenyl bromide using about 3 equivalent of the C-2 lithium or sodium derivative at about −78° C.

In step (b) the formula-XXXVII $\Delta^2$ compounds are formed by oxidative elimination, for example with hydrogen peroxide or sodium periodate.

In steps (c) and (d) the blocking groups are removed to yield the formula-XXXVIII products. In step (c) the thioketal moiety is removed. Any one of several dethioketalization procedures known in the art are useful in this transformation. For example, see reference cited in "Annual Reports in Organic Synthesis 1972", J. McMurry and R. B. Miller, Editors, Academic Press, New York, N.Y., 1973, pages 112–114. Accordingly, a highly useful procedure for this purpose comprises reacting the formula-XXXVIII compound with a mixture of cupric chloride and cupric oxide. The dethioketalization proceeds to completion within several hours, being conveniently monitored by thin layer chromatography, with the reaction being run, for convenience, at ambient temperatures.

In step (d) the blocking groups $R_{30}$ are replaced by hydrogen using mild conditions of hydrolysis. Replacement of $R_{12}$ blocking groups has been described above for Chart A. Silyl groups are readily replaced in a mixture of water and sufficient of a water-miscible organic diluent to give a homogeneous reaction mixture, preferably with a catalytic amount of an organic or inorganic acid. If the silyl group is hindered, such as t-butyldimethylsilyl, the preferred reagent is tetrabutylammonium fluoride. See Corey et al., J. Am. Chem. Soc. 94, 6190 (1972).

Compounds in which $R_1$ is

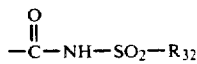

i.e. the N-sulfonylamides, are prepared from the formula-III compounds in their acid form. In Chart G are shown the steps by which those compounds, represented by formula XXXIX, are transformed to the sulfonylamides of formula XLI. In step (a) the acid is converted to a mixed anhydride, here shown as XL, by reaction with isobutylchloroformate in the presence of a tertiary amine such as triethylamine. Other mixed anhydrides are also useful. In step (b) the anhydride is then reacted with the sodium derivative of a sulfonylamide of the formula Na—NH—SO$_2$—R$_{32}$ obtained for example by reaction of methanolic sodium methoxide with an equimolar amount of the sulfonylamide: The reaction step (b) is promoted by the addition of a small amount of hexamethylphosphoramide to insure homogeneity.

The intermediates of Charts A, B, C, and E, including those compounds represented by formulas VI, IX, X, XV, XXIX, XXX, and XXXI are frequently not isolated but used directly for a subsequent process step.

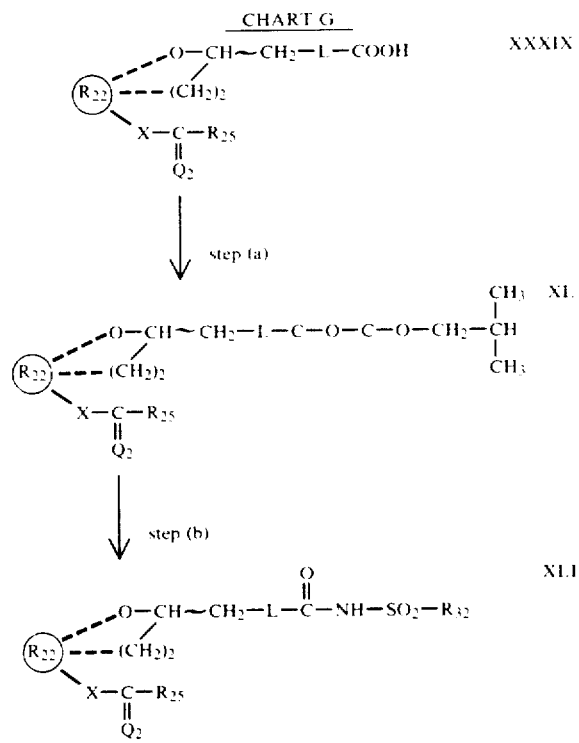

When they are isolated, they are purified by methods known in the art, for example partition extraction, fractional crystallization, and, preferably, silica gel column chromatography.

The compounds of Charts A, B, D, and E wherein Q or Q$_2$ is in either alpha or beta configuration, for example

represent 15-α and 15-β isomers. The transformations shown herein generally have no effect on the stereochemistry at this position and therefore the final products have the same stereo configuration at C-15 as in the starting materials at the corresponding carbon atoms. Should it be necessary to separate 15α and 15β isomers, this can be done by methods known in the art, for example by chromatography on neutral silica gel.

When an optically active intermediate or starting material is employed, subsequent steps yield optically active intermediates or products. That optical isomer of a 4,5-cis-didehydro-PGF$_{1\alpha}$ compound XXXIII is preferred which will yield product III, for example, in the configuration corresponding to that of the naturally occurring prostaglandins. When the racemic form of the intermediate or starting material is employed, the subsequent intermediates or products are obtained in their racemic form. Optically active and racemic forms of the intermediates or starting materials are known or available by methods known in the art.

Compounds within the scope of formula III, herein, occur in two isomeric forms wherein ~ is in alpha or beta configuration, i.e. endo or exo relative to the heterocyclic ring. These two isomers differ in their mobility on TLC silica gel plates or on a silica gel column. The members of each pair of isomers are distinguished herein as "less polar" or "more polar" isomers, considering that mobility.

Blocking groups, $R_{12}$, on formula-III compounds are readily replaced with hydrogen, by acid hydrolysis, for example in dilute acetic acid, aqueous citric acid, or aqueous phosphoric acid-tetrahydrofuran.

When the free acid form of the formula-III compounds is desired, transformation is brought about by methods known in the art, for example saponification.

Esters are conveniently prepared by interaction of the acid with an appropriate diazohydrocarbon, or by interaction of a silver salt of the compound with a alkyl iodide as discussed above.

Substituted phenyl and naphthyl esters are prepared by methods known in the art. See for example U.S. Pat. No. 3,890,372. Phenacyl-type esters are likewise prepared by methods known in the art. See U.S. Pat. No. 3,979,440.

The lower alkanoates of the formula-III compounds disclosed herein are prepared from those compounds by replacing any blocking groups ($R_{12}$) with hydrogen, thereafter subjecting the hydroxy compound to a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 2 to about 10 moles of anhydride per mole of the hydroxy compound reactant. The excess anhydride serves as a reaction diluent and solvent. An inert organic diluent, for example dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride; with acetic anhydride, pyridine, and a 25° C. reaction temperature, a 6 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylate is recovered from the diethyl ether extract by evaporation. The carboxylate is then purified by conventional methods, advantageously by chromatography.

Compounds within the scope of formula III are transformed from one to another by methods known in the art. Accordingly, a compound wherein (R₂₂) is

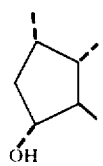

is transformed to another compound wherein (R₂₂) is another ring within the scope of (R₂₂), for example an 11-methylene compound, by methods known or described herein. A compound wherein the $C_{13}$-$C_{14}$ group is trans—CH=CH— is transformed to another compound wherein the $C_{13}$-$C_{14}$ group is cis—CH=CH—, —C≡C—, or —CH$_2$CH$_2$—. For example, —C≡C— is obtained by selective bromination and dehydrobromination. A compound wherein the $C_2$ substituent is —COOR$_{19}$, e.g. a methyl ester, is transformed by known methods to another compound having another $C_2$ substituent within the scope of $R_1$, as defined herein, for example —CH$_2$OH or

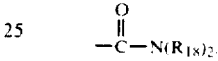

Included among the compounds of formula III are the 11-methylene compounds. Alternate methods for their preparation, other than those included within Charts B, D, and E above wherein (R₂₂) is

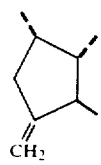

utilize those processes of Charts B, D and E by replacing starting materials XIV, XXIX, and XXXIII with corresponding compounds wherein (R₂₂) is replaced by

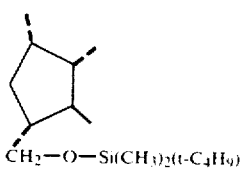

Such compounds are readily prepared from the hydroxymethyl compounds wherein (R₂₂) is

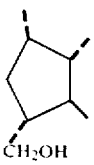

described herein for the starting materials of Chart B, using the procedures of E. J. Corey et al., J. Am. Chem. Soc. 94, 6190 (1970).

Thereafter the procedures of Charts B, D, and E yield compounds bearing the t-butyldimethylsilyloxymethyl group at C-11. It is preferred that $R_{19}$ be alkyl. Next the silyl groups are replaced with hydrogen using tetrabutylammonium fluoride, and the resulting hydroxymethyl groups are converted to iodomethyl groups by way of tosylation and iodide exchange. Finally dehydroiodination, as with potassium tert-butoxide in tetrahydrofuran, yields the 11-methylene compounds.

For all of the reactions described herein, the duration of the reaction is readily determined by monitoring with TLC (thin layer chromatography).

DESCRIPTION OF THE PREFERRED EMBODIMENTS

The invention is further illustrated by, but not limited to, the following examples.

All temperatures are in degrees centigrade.

Reactions are generally run under nitrogen atmosphere supplied from house nitrogen lines.

Infrared absorption spectra are recorded on a Perkin-Elmer model 421 infrared spectrophotometer. Except when specified otherwise, undiluted (neat) samples are used.

The $^1$H NMR spectra are recorded on a Varian A-60, A-60D, T-60, or XL-100 spectrophotometer in deuterochloroform solutions with tetramethylsilane as an internal standard. The $^{13}$C NMR spectra are obtained on a Varian CFT20 spectrometer.

Mass spectra are recorded on a Varian Model MAT CH7 Mass Spectrometer, a CEC Model 110B Double Focusing High Resolution Mass Spectrometer, or a LKB Model 9000 Gas. Chromatograph-Mass Spectrometer (ionization voltage 22 or 70 ev.), and are usually run as TMS (trimethylsilyl) derivatives.

"Brine", herein, refers to an aqueous saturated sodium chloride solution.

"Ether", herein refers to diethyl ether.

"Skellysolve B", herein, refers to mixed isomeric hexanes.

"THP", herein, refers to tetrahydropyran-2-yl.

"TLC", herein, refers to thin layer chromatography.

"HPLC", herein, refers to high pressure liquid chromatography.

"Concentrating", as used herein, refers to concentration under reduced pressure, preferably at less than 50 mm. and at temperatures below 35° C.

"Drying", as used herein, refers to contacting a compound, in solution, with an anhydrous agent such as sodium sulfate or magnesium sulfate to remove water and filtering to remove solids.

Silica gel chromatography, as used herein, is understood to include elution, collection of fractions, and combination of those fractions shown by TLC to contain the desired product free of starting material and impurities.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 247 (1966).

"$R_f$", as used herein, is a term in thin layer chromatography referring to the ratio between the movement of a spot of the sample and that of the solvent front on a silica gel plate (unless otherwise specified) when immersed in a specified solvent.

"More polar" and "less polar" refer to the difference in mobility on TLC silica gel plates or on a silica gel column of two compounds. The members of a pair of isomers may be distinguished as "more polar" or "less polar" isomers, considering that mobility. The less polar one is the faster moving compound, i.e. with greater $R_f$.

"Lower alkanoate", herein, refers to an ester of an alkanoic acid of one to 8 carbon atoms, inclusive.

EXAMPLE 1

9-Deoxy-5ξ,9α-epoxy-2,3-dinor-15(RS)-15-methyl-PGF$_1$, Methyl Ester, less polar isomer and 9-Deoxy-5ξ,9α-epoxy-2,3-dinor-15(RS)-15-methyl-PGF$_1$, Methyl Ester, more polar isomer. (Formula VII)

A. Refer to Chart A. The formula-IX lactol is first prepared. A solution of the 15(RS)-15-methyl lactone, bis-(tetrahydropyran-2-yl) ether of formula VIII (U.S. Pat. No. 3,931,279, 4.24 g.) in 85 ml. of toluene is treated at −70° to 75° C. with diisobutylaluminum hydride (39 ml. of 0.56 M. toluene solution) and stirred for 40 min. Thereafter the reaction mixture is quenched with a saturated aqueous solution of sodium sulfate, mixed with diethyl ether, and filtered. The organic phase is concentrated to an oil containing lactol IX, 4.3 g., having $R_f$ 0.45 (TLC on silica gel in ethyl acetate-Skellysolve B (2:1).

B. A solution of lactol IX (part A above, 4.26 g.) and 2-carboxyethyltriphenylphosphonium chloride (D. B. Denney et al., J. Org. Chem. 27, 3404 (1962), 10.42 g.) in 120 ml. of dimethylsulfoxide-tetrahydrofuran (1:1) is added dropwise to a suspension of sodium hydride (56.28 mmol.) in 20 ml. of the same solvent, cooled in an ice bath. The mixture is stirred at about 25° C. for 66 hr., cooled to about 0° C., quenched with ice water, and acidified to pH 3 with 2N potassium hydrogen sulfate solution. Water and diethyl ether are added and the organic phase is separated, washed with water and brine, dried over anhydrous sodium sulfate, and concentrated. The residue is chromatographed on silica gel, eluting with ethyl acetate-Skellysolve B (1:2) to yield the formula-X compound, as an acid, 3.01 g.

C. The methyl ester of X is obtained by esterification of the above acid with diazomethane in ether-methanol. The resulting product is chromatographed on silica gel, eluting with ethyl acetate-Skellysolve B (1:3) to yield the formula-X mixed isomer bis(tetrahydropyran-2-yl) ether, 2.410 g. having $R_f$ 0.53 (TLC on silica gel in ethyl acetate-Skellysolve B-acetic acid (49:49:2).

D. The formula-VII title compounds are obtained by subjecting the product of part C to acid hydrolysis in 66 ml. of acetic acid-water-tetrahydrofuran (20:10:3) at 40°–45° C. for 4 hr. The solvents are removed by azeotroping with benzene at 40° C./1 mm. The crude product is chromatographed on silica gel, eluting with methylene chloride-acetone (9:1) to yield the formula VII title compounds: 15(RS) less polar isomers, 0.130 g., having $R_f$ 0.46 (TLC on silica gel in acetone-methylene chloride (3:7)); and 15(RS) more polar isomers, 0.160 g., having $R_f$ 0.37 (TLC on silica gel in acetone-methylene chloride (3:7)). The less polar isomers have NMR peaks at 5.55, 3.92, 3.67, 2.90–1.23, 2.48, 1.25, and 0.90 δ; infrared absorption at 3400, 3000, 1750, 1440, 1340, 1295, 1205, 1120, 1055, and 975 cm$^{-1}$; and high resolution mass spectral peak at 298.3179. The more polar isomers have substantially the same values for NMR, infrared, and mass spectral data.

There is also obtained a fraction of much less polar material, 0.619 g. having $R_f$ 0.76 (in acetone-methylene chloride (3:7)), identified as 9,15-dideoxy-5ξ,9α-epoxy- 15-methyl-15,16-trans-didehydro-2,3-dinor-PGF$_1$, methyl ester, represented by the formula

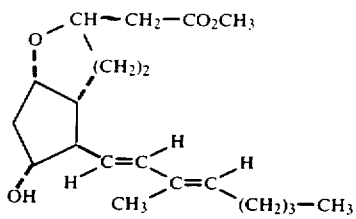

The compound has NMR peaks at 6.38–4.90, 3.95, 3.67, 2.85–1.10, 2.50, 1.70, and 0.90 δ, infrared absorption at 3600, 3000, 1750, 1450, 1300, 1200, 1120, 1058, and 970 cm$^{-1}$, ultraviolet absorption $\lambda max^{EtOH} = 234$ mμ (ε=17,650) and 237 mμ (ε=17,800), and mass spectral lines at 408.2690, 393, 377, 351, and 318.

EXAMPLE 2

9-Deoxy-5ξ,9α-epoxy-PGF$_1$, Methyl Ester, less polar (5R) isomer and more polar (5S) isomer (Formula III)

Refer to Chart E. A solution of mercuric acetate (0.95 g.) in 10 ml. of water is mixed with 10 ml. of tetrahydrofuran. To the resulting suspension is added a solution of formula XXXIII cis-4,5-didehydro-PGF$_{1\alpha}$, methyl ester (0.735 g.) in 10 ml. of tetrahydrofuran dropwise. Stirring is continued at about 25° C. for 4.25 hr. A solution of sodium borohydride (0.200 g.) in 10 ml. of 1 N sodium hydroxide is added dropwise with stirring. After 20 min. brine is added, together with diethyl ether. The organic phase is separated, washed with water, dried over magnesium sulfate, and concentrated to oily product, 0.429 g. The aqueous phase is acidified with dilute hydrochloric acid and extracted with diethyl ether. The organic phase is worked up as above to yield an oil, 0.192 g. which is esterified with diazomethane and combined with the 0.429 g. above. The total product is chromatographed on silica gel, using a high pressure column, and eluted with acetone-(20–30%)-hexane to yield the title compounds: less polar (5R) isomer, 0.349 g., having R$_f$ 0.38 (TLC on silica gel in acetone-methylene chloride (3:7)), and more polar (5S) isomer, 0.144 g., having R$_f$ 0.33 (TLC on silica gel in acetone-methylene chloride (3:7)). The less polar isomer has NMR peaks at 5.49, 3,65, and 0.88 δ, and mass spectral peaks at 512.3320, 497, 441, 422, 412, 391, 351, 325, 235, and 173. The more polar isomer has NMR peaks at 5.50, 3.66, and 0.88 δ, and mass spectral peaks at 512.3331, other peaks as for isomer above.

EXAMPLE 3

9-Deoxy-5ξ,9α-epoxy-PGF$_1$, less polar (5R) isomer (Formula III)

A solution of 9-deoxy-5ξ,9α-epoxy-PGF$_1$, methyl ester, less polar isomer (Example 2, 0.410 g.) in 15 ml. of methanol is treated with 12 ml. of 0.1 N. sodium hydroxide and stirred at about 25° C. for 2 hr., then treated with additional 1 ml. 0.1 N. sodium hydroxide for 3.5 hr. and finally another 2 ml. of 0.1 N. sodium hydroxide for 2.5 hr. The solvent is removed under reduced pressure and the residue acidified to pH<2 with 10% aqueous potassium hydrogen sulfate. The mixture is extracted with ethyl acetate and the combined extracts are washed with water and brine, dried over magnesium sulfate, and concentrated. The residue is chromatographed on silica gel, eluting with ethyl acetate (50–65%)-hexane to yield the title compound, 0.285 g., having R$_f$ 0.53 (TLC on silica gel in ethyl acetate-acetic acid (95:5)); mass spectral peaks at 570.3575, 555, 599, 480, 465, 409, 390, 383, 364, and 173; NMR peaks at 5.53, 4.27–3.60, 1.33, and 0.88 δ; and infrared absorption at 3300 and 1705 cm$^{-1}$.

EXAMPLE 4

9-Deoxy-5ξ,9α-epoxy-PGF$_1$, more polar (5S) isomer (Formula III)

Following the procedure of Example 3 but replacing the methyl ester of that example with the more polar isomer (Example 2, 0.207 g.) there is obtained the title compound, 0.115 g., having R$_f$ 0.40 (TLC on silica gel in ethyl acetate-acetic acid (95:5)); mass spectral peaks at 570.3598, 555, 499, 480, 465, 409, 390, 383, 364, and 173; and NMR and infrared values substantially the same as those for the less polar (5R) isomer of Example 3.

EXAMPLE 5

(5S,15S)- and (5R,15S)-9-Deoxy-5,9α-epoxy-15-methyl-PGF$_1$, Methyl Ester.

Refer to Chart E. Following the procedures of Example 2, but replacing the formula-XXXIII starting material with (15S)-15-methyl-cis-Δ$^4$-PGF$_{1\alpha}$, methyl ester (U.S. Pat. No. 3,954,835, 1.144 g.) there is obtained a mixture of the title compounds. They are separated by silica gel chromatography, using a high pressure column, eluting with acetone (10%)-methylene chloride. The less polar (5R) title compound, 0.75 g., has NMR peaks at 5.52, 4.08–3.70, 3.66, 3.23, 1.27, and 0.88 δ, and a high resolution mass spectral peak at 526.3494. The more polar (5S) title compound, 0.30 g., has NMR peaks at 5.52, 4.20–3.60, 3.68, 1.27, and 0.88 δ.

EXAMPLE 6

(5R, 15S)-9-Deoxy-5,9α-epoxy-15-methyl-PGF$_1$

Following the procedure of Example 3, the (5R) isomer of Example (0.495 g.) is saponified to the title compound, 0.37 g., having NMR peaks at 5.52, 4.10–3.72, 3.23, 1.27 and 0.88 δ, and mass spectral peaks at 584.3712, 569, 513, 494, 479, 423, 404, 397, 378, and 187.

EXAMPLE 7

(5S, 15R)- and (5R, 15R)-9-Deoxy-5,9α-epoxy-15-methyl-PGF$_1$, Methyl Ester.

Refer to Chart E. Following the procedures of Example 2, but replacing the formula-XXXIII starting material with (15R)-15-methyl-cis-Δ$^4$-PGF$_{1\alpha}$, methyl ester (U.S. Pat. No. 3,954,835, 0.82 g.) a mixture of the title compounds is obtained. They are separated by high pressure liquid chromatography as in Example 5, to yield, first, the less polar (5R) title compound, 0.58 g., and second, the more polar (5S) title compound, 0.21 g. The (5R) compound has NMR peaks at 5.52, 4.11–3.50, 3.65, 3.18, and 0.87 δ, and mass spectral peaks at 511.3288, 526, 495, 455, 436, 421, 405, 365, 339, 213, 187 and 143. The (5S) compound has NMR peaks at 5.52, 4.18–3.52, 3.64, and 0.87 δ, and high resolution mass spectral peak at 511.3257 and other peaks similar to those for the (5R) compound.

EXAMPLE 8

(5R, 15R)-9-Deoxy-5,9α-epoxy-15-methyl-PGF$_1$

Following the procedure of Example 3, the (5R) methyl ester of Example 7 (0.25 g.) is saponified to the title compound, 0.20 g., having R$_f$ 0.43 (TLC on silica gel in A-IX system for which see Hamberg et al., J. Biol. Chem. 241, 257 (1966)), NMR peaks at 5.53, 4.14–3.73, 3.24, 1.27, and 0.88 δ, and a high resolution mass spectral peak at 569.3540.

EXAMPLE 9

(5S, 15R)-9-Deoxy-5,9α-epoxy-15-methyl-PGF$_1$

Likewise following the procedure of Example 3, but saponifying the (5S) methyl ester of Example 7, (0.127 g.), the title compound is obtained, 0.103 g., having R$_f$ 0.36 (TLC on silica gel in A-IX), NMR peaks at 5.54, 4.21–3.63, 1.28, and 0.88 δ, and mass spectral peaks at 569.3513, 584, 513, 494, 479, 423, 397, 257, 187, 143, and 117.

EXAMPLE 10

(5S)- and (5R)-9-Deoxy-5,9α-epoxy-16-phenoxy-17,18,19,20-tetranor-PGF$_1$, Methyl Ester.

Refer to Chart E. Following the procedures of Example 2, but replacing the formula-XXXIII starting material with 16-phenoxy-17,18,19,20-tetranor-cis-4,5-didehydro-PGF$_{1\alpha}$, methyl ester (Netherlands Pat. No. 7703950, Derwent Farmdoc Abstract 80703Y, 0.709 g.), a mixture of the title compound is obtained. They are separated by high pressure liquid chromatography as, first, the (5R) title compound, 0.493 g., having R$_f$ 0.44 (TLC on silica gel in acetone-hexane (2:3), NMR peaks at 7.11, 5.67, 4.50, 4.17–3.40, 3.94, 3.63 and 3.17 δ, and mass spectral peaks at 548.2962, 533, 454, 441, 351, and 325. The (5S) title compound, 0.187 g., has R$_f$ 0.32 (TLC on silica gel in acetone-hexane (2:3), NMR peaks at 7.13, 5.68, 4.50, 4.20–3.60, 3.94, and 3.65 δ, and high resolution mass spectral peak at 548.2990.

EXAMPLE 11

(5R)-9-Deoxy-5,9α-epoxy-16-phenoxy-17,18,19,20-tetranor-PGF$_1$

Following the procedure of Example 3, the (5R) methyl ester of Example 10 (0.292 g.) is saponified to the title compound, 0.278 g., white solids. An analytical sample is obtained on recrystallization from ethyl acetate-hexane, m.p. 45°–47° C., having R$_f$ 0.66 (TLC on silica gel in acetic acid (5%)-ethyl acetate), NMR peaks at 7.12, 5.68, 4.50, 4.21–3.67, 3.94, and 3.18 δ, and mass spectral peaks at 606.3196, 591, 512, 499, 409, 383, and 243.

EXAMPLE 12

(5S)-9-Deoxy-5,9α-epoxy-16-phenoxy-17,18,19,20-tetranor-PGF$_1$

Likewise following the procedure of Example 3, the (5S) methyl ester of Example 10 (0.18 g.) is saponified to the title compound, 0.158 g., having R$_f$ 0.50 (TLC on silica gel in acetic acid (5%)-ethyl acetate), NMR peaks at 7.12, 5.68, 4.50, 4.28–3.58, and 3.94 δ, and mass spectral peaks at 606.3202, 591, 516, 512, 499, 409, 383, 319, and 243.

EXAMPLE 13

(2E, 5S)-9-Deoxy-5,9α-epoxy-Δ$^2$-PGF$_1$, Methyl Ester

The preparation of the title compound is based on the dehydrohalogenation of (4S, 5S)-4-halo-9-deoxy-5,9α-epoxy-PGF$_1$, methyl ester which is first obtained as follows.

I. A solution of iodine in methylene chloride (112 ml., 2.5%, 10.9 mmols) is added dropwise (35 min.) at room temperature to a stirred mixture of cis-Δ$^4$-PGF$_{1\alpha}$, methyl ester (U.S. Pat. No. 3,954,835, 2.01 g., 5.45 mmole) dissolved in methylene chloride (260 ml.) and a saturated aqueous solution of sodium bicarbonate (92 ml.). The reaction is worked up after 2 hr. by first adding methylene chloride (1300 ml.) and then shaking with aqueous 0.2M sodium thiosulfate solution (80 ml.). The layers are separated quickly and the organic layer washed successively with water (360 ml.), pH 2 buffer (140 ml.), and water (360 ml.). Following drying over magnesium sulfate, the organic layer is concentrated and the residue chromatographed over three Merck B HPLC columns. Eluting with acetone-hexane (1:3) yields first (4S, 5S)-4-iodo-9-deoxy-5,9α-epoxy-PGF$_1$, methyl ester (1.215 g.), as a colorless oil, R$_f$ 0.38 (TLC on silica gel in acetone-hexane (40:60)); and having mass spectral peaks (TMS derivative) at 638.2308, 623, 567, 548, 517, 511, 477, 451, and 173; $^1$H NMR signals at 5.50, 3.98, 3.67, and 0.88 δ (CDCl$_3$); $^{13}$C NMR signals at 173.0, 135.3, 132.4, 79.6, 79.0, 78.1, 72.8, 52.5, 51.6, 42.7, 41.3, 37.1, 34.0, 32.2, 31.7, 25.9, 25.2, 22.6, 21.7, and 14.0 δ (CDCl$_3$).

II. A solution of the above (4S, 5S)-4-iodo-9-deoxy-5,9α-epoxy-PGF$_1$, methyl ester (1.126 g.) in 60 ml. of toluene is treated under nitrogen with 2.5 ml. of 1,5-diazabicyclo[4.3.0]non-5-ene (DBN) at 40°–45° C. for 72 hr. The mixture is cooled to about 25° C., diluted with toluene, washed with water, dried, and concentrated to an oil, 0.832 g. A solution of the il in 15 ml. of tetrahydrofuran is treated with 15 ml. of buffer solution (pH 1.5) and stirred at about 25° C. for 1.5 hr. The mixture is then diluted with ethyl acetate and washed with brine. The organic phase is washed with water, dried, and concentrated to an oil. The oil is chromatographed over three Merck B HPLC columns, eluting with acetone (20–50%)-hexane, to yield, first, the title compound, 0.369 g. having R$_f$ 0.55 (TLC on silica gel in acetone (30%)-methylene chloride), NMR peaks at 6.95, 5.85, 5.50, 3.70, 3.33, and 0.88 δ, and mass spectral peaks at 510.3188, 495, 479, 439, 420, 411, 349, 323, 199, and 173.

There is also obtained in subsequent fractions 5-oxo-PFG$_{1\alpha}$, methyl ester, 0.094 mg., having R$_f$ 0.21 (TLC on silica gel in acetone (30%)-methylene chloride).

EXAMPLE 14

(5R)-9-Deoxy-5,9α-epoxy-PFG$_1$, p-Phenylphenacyl Ester

A solution of (5R)-9-deoxy-5,9α-epoxy-PGF$_1$ (Example 3, 0.708 g.) in 30 ml. of acetonitrile is treated with diisopropylethylamine (1.4 ml.) and p-phenylphenacyl-bromide (1.0 g.) at about 25° C. for 1.5 hr. The mixture is concentrated to one-third its volume, diluted with brine (20 ml.) and aqueous 10% citric acid (20 ml.), and extracted with ethyl acetate. The organic phase is washed with brine, dried, and concentrated. The product is chromatographed on silica gel, first removing unreacted p-phenylphenacyl bromide, then eluting with acetone (60%)-hexane to yield the title compound, 1.02 g. An analytical sample is obtained on recrystallization from acetone-hexane, m.p. 103°-104° C., having $R_f$ 0.57 (TLC on silica gel in acetone (40%)-hexane), NMR peaks at 7.79, 7.49, 5.49, 5.32, 4.21-3.65, 3.25, and 0.88 δ, and mass spectral peaks at 621.3080, 692, and 677.

EXAMPLE 15

(5S)-9-Deoxy-5,9α-epoxy-PGF$_1$, p-Phenylphenacy Ester

Following the procedures of Example 14 but starting with (5S)-9-deoxy-5,9α-epoxy-PGF$_1$ (Example 4, 0.354 g.) there is obtained the title compound, 0.325 g. Recrystallization gives an analytical sample, m.p. 97°-98° C., having $R_f$ 0.45 (TLC on silica gel in acetone (40%)-hexane), NMR peaks at 7.79, 7.49, 5.48, 5.33, 4.23-3.55 and 0.88 δ, and mass spectral peaks at 621.3055, 692, and 677.

EXAMPLE 16

(5S)- and (5R)-9-Deoxy-5,9α-epoxy-PGF$_1$, Amide

A mixture of the (5S)- and (5R)-9-deoxy-5,9α-epoxy-PGF$_1$, methyl esters (Example 2) is saponified in methanol with 0.1 N. sodium hydroxide at about 25° C. for 8 hr. followed by the usual work-up to give a mixture of the free acids. A solution of the (5S)- and (5R)-9-deoxy-5,9α-epoxy-PGF$_1$ (0.645 g.) in 10 ml. of acetone is treated with triethylamine (0.4 ml.) and cooled to −5° C. Then isobutylchloroformate (0.38 ml.) is added and the mixture is stirred for 10 min. There is then added 10 ml. of a saturated solution of ammonia in acetonitrile and the mixture stirred at −5° C. for 10 min. The reaction mixture is diluted with brine (100 ml.) and water (20 ml.) and extracted with ether. The organic phase is washed with brine and 2 N. hydrochloric acid, then with brine and 5% sodium bicarbonate, and finally brine, then dried and concentrated to crude product, 0.510 g. A similar preparation derived from half the above quantities is combined and the resulting 0.765 g. is chromatographed on a HPLC silica gel column, eluting with acetone. There are obtained (a) undesired material, 0.190 g., (b) the (5R) title compound, 0.285 g., (c) a mixture of (5S) and (5R) compounds (0.04 g.), and (d) the (5S) title compound, 0.110 g. The (5R) title compound has $R_f$ 0.34 (TLC on silica gel in acetone), NMR peaks at 5.50, 4.20-3.68, 3.27, and 0.90 δ, and mass spectral peaks at 569.3738, 554, 498, 479, 470, 464, 408, 389, 382, 335, 318, and 173. The (5S) title compound has $R_f$ 0.24 (TLC on silica gel in acetone), NMR peaks at 5.50, 4.20-3.58, and 0.88 δ and high resolution mass spectral peak at 569.3744.

EXAMPLE 17

(5R)-9-Deoxy-5,9α-epoxy-PGF$_1$, Methyl Ester (Formula III)

I. Refer to Chart B. There is first prepared (4S,5S)-4-iodo-9-deoxy-5,9α-epoxy-PGF$_1$, methyl ester (formula XV) following the procedure of Example 13-I. The desired compound is eluted in less polar fractions, having $R_f$ 0.38 (in acetone-hexane (40:60)).

Subsequent to the above compound there is eluted the corresponding more polar (4R,5R)-4-iodo isomer (0.440 g.), m. 72°-74° C. (from etherhexane), having $R_f$ 0.32 (in acetone-hexane (40:60)), mass spectral peaks at 638.2346, 623, 607, 567, 517, 511, 477, 451, 421, and 173; proton NMR peaks at 5.49, 4.34, 4.10, 3.67, and 0.88 δ; $^{13}$C NMR peaks at 173.0, 135.8, 132.6, 75.9, 73.0, 71.3, 54.4, 51.7, 41.6, 40.0, 37.0, 34.2, 31.7, 31.2, 25.2, 24.4, 22.6, 20.7, and 1.40 δ; and infrared absorption at 3400, 1740, 1715, and 965 cm$^{-1}$.

II. The formula-XV (4S,5S)-iodo compound is next reduced to the formula-III title compound. A solution of the above (4S,5S) compound (0.29 g.) in 15 ml. of methanol is treated, while stirring, first with 0.5 ml. of tri-n-butyltin chloride and then portions of solid sodium borohydride (0.3 g. total) added over 5 min. The mixture stirred one hr. at about 25° C., then poured into 75 ml. of brine and extracted with ethyl acetate. The organic phase is washed with brine, dried, and concentrated. The residue is chromatographed on silica gel, eluting with acetone-hexane (1:3) to yield the title compound, 0.17 g. having identical properties to those of the less polar product of Example 2.

EXAMPLE 18

(5S)-9-Deoxy-5,9α-epoxy-2-phenylselenidyl-PGF$_1$, Methyl Ester, 11,15-bis(tetrahydropyranyl ether) (Formula-XXXVI)

I. Refer to Chart F. The formula-XXXV THP-blocked compound is first prepared. A solution of (5R)-9-deoxy-5,9α-epoxy-PGF$_1$, methyl ester (Example 17, 0.749 g.) in 20 ml. of methylene chloride is treated with dihydropyran (1.86 ml.) and pyridine hydrochloride (0.040 g.) at about 25° C. for 23 hr. The mixture is diluted with methylene chloride, washed with aqueous sodium bicarbonate (10%), and brine, dried and concentrated to the bis(THP) ether (formula XXXV).

II. The above product, in 2 ml. of tetrahydrofuran, is treated at −78° C. with the lithium amide prepared from N,N-diisopropylamine (0.658 g.) in tetrahydrofuran at −78° C. with n-butyllithium (2.8 ml. of 2.2 M in hexane). The mixture is stirred at −78° C. for 1.5 hr., then treated with diphenyl diselenide (0.811 g.) in 4 ml. of tetrahydrofuran, added dropwise. The mixture is stirred an additional hour at −78° C., warmed to about 25° C., and added to saturated aqueous ammonium chloride solution (30 ml.). The mixture is extracted with ether and the organic phase is washed with water and brine, dried, and concentrated to an oil, 1.96 g. This residue is chromatographed by HPLC, eluting with ethyl acetate (10-20%)-toluene to yield the title compound, 0.646 g., having NMR peaks at 7.49, 5.49, 4.72, 3.63, and 0.87 δ.

EXAMPLE 19

(2E,5S)-9-Deoxy-5,9α-epoxy-2,3-didehydro-PGF$_1$, Methyl Ester, 11,15-bis(tetrahydropyranyl ether) (Formula XXXVII)

Refer to Chart F. A solution of the formula-XXXVI phenylselenide (Example 18, 0.634 g.) in 20 ml. of methylene chloride is treated with 30% hydrogen peroxide-water (1.6 ml. :2.4 ml.) added dropwise over 2 min. and stirred for 2 hr. at about 25° C. The mixture is diluted with methylene chloride and shaken with 20 ml. of 5% aqueous sodium bicarbonate. The organic phase is washed with 25 ml. of 10% aqueous sodium bicarbonate, water, and brine, dried, and concentrated to the title compound, 0.504 g., having $R_f$ 0.57 (in ethyl acetate (20%)-benzene).

EXAMPLE 20

(2E,5S)-9-Deoxy-5,9α-epoxy-2,3-didehydro-PGF$_1$, Methyl Ester (Formula XXXVIII).

Refer to Chart F. The formula-XXXVII compound, namely (2E,5S)-9-deoxy-5,9α-epoxy-2,3-didehydro-PGF$_1$, methyl ester, 11,15-bis(tetrahydropyranyl ether) (Example 19, 0.504 g.) is deblocked in 20 ml. of acetic acid-water-tetrahydrofuran (20:10:3) at 40° C. for 4 hr. Solvents are removed azeotropically with toluene. The residue is chromatographed by HPLC, eluting with acetone (25–30%)-hexane, to yield the title compound, 0.205 g., having R$_f$ 0.49 (in acetone (40%)-hexane) and NMR spectral lines identical to those of the product of Example 13.

EXAMPLE 21

(2E,5S)-9-Deoxy-5,9α-epoxy-2,3-didehydro-PGF$_1$ (Formula-III wherein L is —CH=CH— and R$_1$ is —COOH A solution of the formula-XXXVIII methyl ester of (2E,5S)-9-deoxy-5,9α-epoxy-2,3-didehydro-PGF$_1$ (Example 20, 0.383 g.) in 14 ml. of t-butanol is treated with 3.5 ml. of 3 N aqueous potassium hydroxide and stirred at about 25° C. for 24 hr. There is added 60 ml. of ice water and 12 ml. of 2 M aqueous sodium hydrogen sulfate and the mixture is extracted with ether. The organic phase is washed with brine, dried, and concentrated to an oil, 0.386 g. The residue is chromatographed on Mallinkrodt CC4 acid-washed silica gel, eluting with ethyl acetate (50–100%)-hexane to yield the title compound, an oil, 0.286 g., having R$_f$ 0.22 (hexane-ethyl acetate-acetic acid (50:45:5)), mass spectral peak at 568.3425, and NMR peaks at 7.04, 5.86, 5.49, 3.92, 3.37, and 0.88 δ.

EXAMPLE 22

(5R)-9-Deoxy-5,9α-epoxy-2-phenylselenidyl-PGF$_1$, 11,15-bis[(t-butyldimethyl)silyl ether], Methyl Ester (Formula-XXXVI).

I. Refer to Chart F. The formula-XXXV silyl-blocked compound is first prepared. A solution of (5S)-9-deoxy-5,9α-epoxy-PGF$_1$, methyl ester (Example 2, 0.928 g.) in 9 ml. of dimethylformamide is treated at about 0°–5° C. with imidazole (0.412 g.) and t-butyldimethylsilyl chloride (0.797 g.). The mixture is stirred at about 25° C. for one hr., then treated with additional imidazole (0.026 g.) and t-butyldimethylsilyl chloride (0.399 g.). The mixture is stirred for 17 hr., then added to 60 ml. of ice water and extracted with ether. The organic phase is washed with water and brine, dried, and concentrated to an oil, 1.46 g. having R$_f$ 0.53 (in ethyl acetate (4%)-toluene).

II. The above product, in 3 ml. of tetrahydrofuran, is treated at −78° C. with the lithium amide prepared from N-cyclohexyl-N-isopropylamine (1.107 g.) in 6 ml. of tetrahydrofuran at −78° C. with n-butyllithium (4.6 ml. of 1.6 M in hexane). The mixture is stirred at −78° C. for 1.75 hr., then treated at −78° C. with diphenyl diselenide (0.980 g.) in 5 ml. of tetrahydrofuran, added dropwise over 4 min., stirred at −78° C. for one hr., and then warmed to about 25° C. The mixture is added to 40 ml. of saturated aqueous ammonium chloride solution and extracted with ether. The organic phase is washed with water and brine, dried, and concentrated. The residue is chromatographed by HPLC eluting with acetone (5–10%) to yield the formula-XXXVI title compound, 1.142 g., having R$_f$ 0.65 (in ethyl acetate (4%))toluene), and NMR peaks at 7.42, 5.44, 4.26–3.48, 3.61, and 0.87 δ.

EXAMPLE 23

(2E,5R)-9-Deoxy-5,9α-epoxy-2,3-didehydro-PGF$_1$, Methyl Ester, 11,15-bis[(t-butyldimethyl)silyl ether] (Formula XXXVII)

Refer to Chart F. A solution of the formula-XXXVI phenylselenide (Example 22, 1.142 g.) in 30 ml. of methylene chloride is treated with 30% hydrogen peroxide-water (3.9 ml.:2.6 ml.) added dropwise over 4 min. and stirred for 2 hr. at about 25° C. The mixture is diluted with methylene chloride and shaken with 30 ml. of 5% aqueous sodium bicarbonate. The organic phase is washed with 30 ml. of 10% aqueous sodium bicarbonate, water, and brine, dried and concentrated to the title compound, having R$_f$ 0.53 (in ethyl acetate (4%)-toluene).

EXAMPLE 24

(2E,5R)-9-Deoxy-5,9α-epoxy-2,3-didehydro-PGF$_1$, Methyl Ester Ester (Formula XXXVIII)

Refer to Chart F. The formula-XXXVII compound, namely (2E,5R)-9-deoxy-5,9α-epoxy-2,3-didehydro-PGF$_1$, methyl ester, 11,15-bis[(t-butyldimethyl)silyl ether] (Example 23) is deblocked in 16 ml. of acetic acid-water-tetrahydrofuran- 1 N hydrochloric acid (3:1:1:0.08) with stirring at about 25° C. for 3 hr. Brine and ethyl acetate are added and the aqueous phase is extracted with ethyl acetate. The combined organic phase is washed with water and brine, dried and concentrated to an oil which crystallizes, 0.624 g. This residue is chromatographed by HPLC on 3 Merck B columns, eluting with acetone (25–40%)-hexane to yield 0.426 g. An analytical sample, recrystallized from ether-pentane, has m.p. 74.5°–75.5° C., R$_f$ 0.27 (in acetone (40%)-hexane), mass spectral lines at 510, 495, 439, 349, 321, and 173, and NMR peaks at 6.96, 5.89, 5.50, 4.26–3.20, 3.72, and 0.88 δ.

EXAMPLE 25

(2E,5R)-9-Deoxy-5,9α-epoxy-2,3-didehydro-PGF$_1$ (Formula-III) wherein L is —CH=CH— and R$_1$ is —COOH A solution of the formula-XXXVIII methyl ester of (2E,5R)-9-deoxy-5,9α-epoxy-2,3-didehydro-PGF$_1$ (Example 24, 0.305 g.) in 10 ml. of t-butanol is treated with 2.7 ml. of 3 N potassium hydroxide and stirred at about 25° C. for 17 hr. The mixture is treated with 60 ml. of ice water and 15 ml. of 2 M sodium hydrogen sulfate and extracted with ethyl acetate. The organic phase is washed with brine, dried, and concentrated to a waxy solid, 0.279 g. The residue is chromatographed on Merck CC4 acid-washed silica gel, eluting with ethyl acetate (50–100%)-hexane to yield the title compound, 0.251 g. An analytical sample when crystallized has m.p. 66°–69° C., R$_f$ 0.20 (in hexane-ethyl acetate-acetic acid (50:45:5)), mass spectral lines at 568, 553, 497, 478, 437, 407, and 321, and NMR peaks at 7.05, 5.90, 5.52, 4.33–3.66 and 0.88 δ.

EXAMPLE 26

(5R)-9-Deoxy-5,9α-epoxy-13,14-dihydro-PGF$_1$, Methyl Ester (Formula III) wherein X is —CH$_2$CH$_2$ A solution of the methyl ester of (5R)-9-deoxy-5,9α-epoxy-PGF$_1$, (Example 2, less polar isomer, 1.351 g.) in 150 ml. of 95% ethanol is hydrogenated at atmospheric pressure at 18° C. in the presence of palladium (10%)-on-carbon (150 mg.) and sodium nitrite (40 mg.). The mixture is filtered and concentrated to an oil. The preparation is repeated on one-eighth scale. The combined oils are chromatographed by HPLC, eluting with acetone (20%)-hexane to yield two products, the less polar being the ethyl ester of (5R)-9-deoxy-5,9α-epoxy-13,14-dihydro-PGF$_1$, 0.604 g. having R$_f$ 0.67 (in ethyl acetate (75%)-hexane) and NMR peaks at 4.12, 4.05–3.37, 3.17, 2.31, 1.25, and 0.88 δ. The other, more polar, product is the title compound, 0.650 g. having NMR peaks at 4.05–3.37, 3.66, 3.21, 2.33, and 0.89 δ and mass spectral peaks at 5.14.3491, 443, 424, 353, and 173.

EXAMPLE 27

(5R)-9-Deoxy-5,9α-epoxy-13,14-dihydro-PGF$_1$

A solution of the ethyl ester (Example 26, 0.65 g.) in 29 ml. of methanol is treated with 34 ml. of 0.1 N sodium hydroxide at about 25° C. for 2 hr. The mixture is partially concentrated, acidified with 10% potassium hydrogen sulfate solution, and extracted with ethyl acetate. The organic phase is washed with brine, dried, and concentrated to the title compound, having R$_f$ 0.23 (in hexane-ethyl acetate-acetic acid (50:45:5), NMR peaks at 5.64, 3.91, 3.63, 3.21, 2.35, and 0.89 δ, and mass spectral peaks at 572.3731, 501, 482, 411, 392, and 173.

EXAMPLE 28

(5S)-9-Deoxy-5,9α-epoxy-2-phenylselenidyl-13,14-dihydro-PGF$_1$, 11,15-bis[(t-butyldimethyl)silyl ether], Methyl Ester (Formula XXXVI)

I. Refer to Chart F. The formula-XXXV silyl-blocked compound is first prepared, following the procedures of Example 22. A solution of (5R)-9-deoxy-5,9α-epoxy-13,14-dihydro-PGF$_1$, methyl ester (Example 26, 0.830 g.) in 9 ml. of dimethylformamide is treated at about 0°–5° C. with imidazole (0.367 g.) and t-butyldimethylsilyl chloride (0.705 g.). The mixture is stirred at about 25° C. for 19 hr., then treated with additional imidazole (0.183 g.) and t-butyldimethylsilyl chloride (0.352 g.) and stirred for 5 hr. Still additional amounts of imidazole (0.183 g.) and t-butyldimethylsilyl chloride (0.352 g.) are added and stirring continued for 16 hr., until the reaction is considered complete by TLC. The mixture is added to ice water (60 ml.) and extracted with ether. The organic phase is washed with water and brine, and concentrated to an oil (1.31 g.) having R$_f$ 0.71 (in acetone (20%)-hexane) and NMR peaks at 4.00–3.49, 3.65, and 0.90 δ.

II. The above product (1.31 g.) in 2 ml. of tetrahydrofuran is added dropwise to the lithium amide prepared from N-cyclohexyl-N-isopropylamine (0.994 g.) in 5.4 ml. of tetrahydrofuran at −78° C. with n-butyllithium (4.1 ml. of 1.6 M in hexane). The mixture is stirred at −78° C. for 1.5 hr., then treated at −78° C. with diphenyl diselenide (0.873 g.) in 4 ml. of tetrahydrofuran, added dropwise over 4 min., stirred at −78° C. for one hr., and then warmed to about 25° C. The mixture is added to 30 ml. of saturated aqueous ammonium chloride solution and extracted with ether. The organic phase is washed with water and brine, dried, and concentrated. The residue (2.04 g.) is chromatographed by HPLC, eluting with ethyl acetate (4%)-toluene to yield the title compound as two isomers having R$_f$ 0.65 and 0.61 (in ethyl acetate (5%)-toluene), combined weight 0.864 g., having NMR peaks at 7.43, 3.91–3.44, 3.58, and 0.88 δ.

EXAMPLE 29

(2E,5S)-9-Deoxy-5,9α-epoxy-2,3-didehydro-13,14-dihydro-PGF$_1$, Methyl Ester, 11,15-bis[(t-butyldimethyl)silyl ether] (Formula XXXVII)

Refer to Chart F. A solution of the formula-XXXVI phenylselenide (Example 28, 0.987 g.) in 30 ml. of methylene chloride is treated with 30% hydrogen peroxide-water (3.9 ml.:2.6 ml.) added dropwise and stirred at about 25° C. for 2.25 hr. The mixture is diluted with methylene chloride and shaken with 5% aqueous sodium bicarbonate. The organic phase is washed with 10% aqueous sodium bicarbonate, water, and brine, dried, and concentrated to the title compound, 0.768 g., having R$_f$ 0.46 (in ethyl acetate (4%)-toluene).

EXAMPLE 30

(2E,5S)-9-Deoxy-5,9α-epoxy-2,3-didehydro-13,14-dihydro-PGF$_1$, Methyl Ester (Formula XXXVIII)

Refer to Chart F. The formula-XXXVII compound, namely (2E,5S)-9-deoxy-5,9α-epoxy-2,3-didehydro-13,14-dihydro-PGF$_1$, methyl ester, 11,15-bis[(t-butyldimethyl)silyl ether] (Example 29, 0.768 g.) is treated with 15 ml. of acetic acid-water-tetrahydrofuran-1 N hydrochloric acid (3:1:1:0.08) with stirring at about 25° C. for 4.5 hr. Brine (20 ml.) and water (20 ml.) are added and the mixture is extracted with ethyl acetate. The organic phase is washed with water, saturated aqueous sodium bicarbonate, water, and brine, dried, and concentrated to 0.545 g., having R$_f$ 0.09 (in acetone (20%)-hexane). The residue is chromatographed by HPLC to yield the title compound, 0.374 g., having NMR peaks at 6.98, 5.87, 4.07–3.16, 3.72, 2.37, and 0.90 δ, and mass spectral peaks at 512, 497, 441, 422, 351, and 173.

EXAMPLE 31

(2E,5S)-9-Deoxy-5,9α-epoxy-2,3-didehydro-13,14-dihydro-PGF$_1$ (Formula III) wherein L is —CH=CH— and R$_1$ is —COOH Following the procedures of Example 25 the formula-XXXVIII methyl ester of (2E,5S)-9-deoxy-5,9α-epoxy-2,3-didehydro-13,14-dihydro-PGF$_1$ (Example 30, 0.262 g.) is transformed to the acid, 0.279 g. The oily product is chromatographed on Merck CC4 acid-washed silica gel, eluting with ethyl acetate (40–60%)-hexane to yield the title compound, 0.180 g., having R$_f$ 0.49 (in A-IX), NMR peaks at 7.05, 5.86, 4.13–3.13, 2.38, and 0.89 δ, and mass spectral peaks at 570, 555, 499, 480, 413, 409, 323, and 233.

EXAMPLE 32

(2E,5S)-9-Deoxy-5,9α-epoxy-2,3-didehydro-13,14-dihydro-PGF$_1$, N-Methanesulfonylamide A solution of the acid, namely (2E,5S)-9-deoxy-5,9α-epoxy-2,3-didehydro-13,14-dihydro-PGF$_1$ (Example 31, 0.150 g.) in 5 ml. of tetrahydrofuran is treated at 0° C. with triethylamine (0.047 g.) and isobutylchloroformate (0.064 g.) for one hr. There is then added the sodium derivative of methanesulfonamide (prepared from 190 mg. of methanesulfonamide and 0.42 ml. of 4.4 N sodium methoxide in methanol), in solid form, followed by 2 ml. of dimethylsulfoxide to bring into solution. The mixture is stirred at about 25° C. for 17 hr., then acidified with ice-cold dilute hydrochloric acid. The solution is extracted with ethyl acetate and the organic phase is washed with water and brine, dried, and concentrated. The residue, 0.219 g., is chromatographed on acid-washed silica gel, eluting with ethyl acetate (50–100%)-hexane, to yield the title compound. Further treatment in ether, washing with water, yields 0.131 g., which when rechromatographed yields 0.093 g., having $R_f 0.56$ (in ethyl acetate-acetic acid 95:5) and mass spectral lines at 632.3267, 576, 568, 557, 486, 478, and 173.

EXAMPLE 33

(5S)-9-Deoxy-5,9α-epoxy-13,14-dihydro-PGF$_1$, Methyl Ester (Formula III) wherein X is —CH$_2$CH$_2$ A solution of the methyl ester of (5S)-9-deoxy-5,9α-epoxy-PGF$_1$ (Example 2, more polar isomer, 3.18 g.) in 200 ml. of methanol is hydrogenated at atmospheric pressure in the presence of 400 mg. of platinum oxide and 95 mg. of sodium nitrite. The reaction is complete in 1.5 hr. and the mixture is then filtered and concentrated. The residue is taken up in ethyl acetate. The solution is washed with water, dried, and concentrated to 2.90 g. The residue is chromatographed, eluting with acetone (20–25%)-hexane, to yield the title compound, 2.35 g., having $R_f 0.30$ (in ethyl acetate (75%)-hexane).

EXAMPLE 34

(2E,5R)-9-Deoxy-5,9α-epoxy-2,3-didehydro-13,14-dihydro-PGF$_1$, Methyl Ester (Formula XXXVIII)

I. Refer to Chart F. Following the procedure of Examples 28–30, there is first prepared the formula-XXXV silyl-blocked compound, replacing the starting material with (5S)-9-deoxy-5,9α-epoxy-13,14-dihydro-PGF$_1$, methyl ester of Example 33.

II. The above product is converted to the formula-XXXVI phenylselenide- following the procedures of Example 28-II, to yield 2.601 g. as two isomers having $R_f 0.57$ and 0.49 (in ethyl acetate (4%)-toluene).

III. The phenylselenide is transformed to the formula-XXXVIII 2,3-didehydro title compound following the procedures of Examples 29 and 30. There is first obtained the formula XXXVII compound, namely (2E,5R)-9-deoxy-5,9α-epoxy-2,3-didehydro-13,14-dihydro-PGF$_1$, methyl ester, 11,15-bis[(t-butyldimethyl)silyl ether].

EXAMPLE 35

(5R)-9,15-Dideoxy-5,9α-epoxy-13,14-dihydro-PGF$_1$, methyl ester and acid

I. There is first prepared cis-Δ$^4$-PGF$_1$α, methyl ester, 15-(t-butyldimethyl)silyl ether. Applying the techniques of Johnson et al., J. Am. Chem. Soc. 99, 7738 (1977), cis-Δ$^4$-PGF$_1$α, methyl ester (U.S. Pat. No. 3,954,835, 6.40 g.) and 1-butaneboronic acid (1.97 g.) are heated in benzene (425 ml.) at reflux, removing water azeotropically with a Dean-Stark trap. After 3 hr., 30 ml. of dimethylformamide is added and the mixture refluxed an additional 0.5 hr. The mixture is cooled and treated with imidazole (4.69 g.) and t-butyldimethylsilyl chloride (5.19 g.). Using reduced pressure, the benzene is removed. The remaining solution is stirred at about 25° C. for 16 hr. There is then added acetone (250 ml.), sodium bicarbonate (1.9 g.) and aqueous 30% hydrogen peroxide (55 ml.) and the mixture is stirred at about 25° C. for 6.5 hr. Water (250 ml.) is added and reduced pressure applied to remove acetone. The solution is extracted with ethyl acetate and the organic phase is washed with water, dried, and concentrated to 7.72 g.

II. Next the above compound is cyclized by the mercuration-demercuration procedure. The above product (7.72 g.) in 90 ml. of tetrahydrofuran is added to mercuric acetate in water-tetrahydrofuran (prepared by addition of a solution of mercuric acetate (6.43 g.) in 90 ml. of water to 90 ml. of tetrahydrofuran, stirred at about 25° C. for 0.5 hr.) and stirred at about 25° C. for 5 hr. or until complete as monitored by TLC. The mixture is cooled in an ice bath and treated with solid sodium borohydride (1.46 g.) added in portions. Brine (180 ml.) is added and the mixture extracted with ether. The organic phase is washed with water and brine, dried, and concentrated. The residue (7.29 g.) is chromatographed, eluting with ethyl acetate (25%)-hexane, to yield (1) (5R)-9-deoxy-5,9α-epoxy-PGF$_1$, methyl ester, 15-(t-butyldimethyl)silyl ether, 3.91 g. having $R_f 0.43$ (in ethyl acetate (30%)-hexane, NMR peaks at 5.46, 3.70–4.25, 3.63, 3.20, 2.34, 2.30, and 0.87 δ, and (2) (5S)-9-deoxy-5,9α-epoxy-PGF$_1$, methyl ester, 15-(t-butyldimethyl)silyl ether, 1.50 g. having NMR peaks at 5.47, 3.60–4.25, 3.65, 2.35, and 0.88 δ.

III. The above (5R) compound is reduced catalytically to a mixture of the 13,14-dihydro compound and the title methyl ester 15-deoxy compound. A solution of the above (5R) compound (1.20 g.) in 60 ml. of ethyl acetate together with 120 mg. of 5% palladium-on-charcoal catalyst is hydrogenated at atmospheric pressure for 55 min. The mixture is then filtered and concentrated to an oil, 1.16 g. Product from a similar preparation of one-tenth scale is combined and chromatographed by HPLC, eluting with ethyl acetate (15–20%)-hexane to yield (1) (5R)-9-deoxy-5,9α-epoxy-13,14-dihydro-PGF$_1$, methyl ester, 15-(t-butyldimethyl)silyl ether, 0.912 g., having $R_f 0.51$ (in ethyl acetate (30%)-hexane), NMR peaks at 4.06–3.13, 3.68, 3.13, 2.39, 2.35, and 0.91 δ and mass spectral peaks at 499.3300, 541, 525, 485, 424, 409, and 215, and (2) the title methyl ester compound, namely (5R)-9,15-dideoxy-5,9α-epoxy-13,14-dihydro-PGF$_1$, methyl ester, 0.171 g., having $R_f 0.41$ (in ethyl acetate (30%)-hexane), NMR peaks at 4.05–3.59, 3.68, 3.20, 2.33, and 0.89 δ, and mass spectral peaks at 426.3179, 411, 408, 395, 336 and 325.

IV. The title acid compound is obtained by saponification of the methyl ester. A solution of the above 15-deoxy compound (0.205 g.) in 5 ml. of methanol is treated with 3 ml. of 0.5 N. aqueous sodium hydroxide solution and stirred at about 25° C. for 4 hr. The mixture is partially concentrated and then acidified to pH 2 with 2 M sodium hydrogen sulfate, also diluting with ethyl acetate. The organic phase is washed with brine-water (1:1), dried, and concentrated. The residue is chromatographed on Mallinkrodt CC4 acid-washed silica gel, eluting with ethyl acetate (25%)-hexane to yield the desired acid 0.161 g., having NMR peaks at 3.85, 3.21, 2.33, and 0.88 δ and high resolution mass spectral peak at 484.3389.

EXAMPLE 36

(5R)- and
(5S)-9-Deoxy-5,9α-epoxy-16-(3-chlorophenoxy)-17,18,19,20-tetranor-PGF$_1$, Methyl Ester Refer to Chart E. Following the procedures of Example 2, but replacing the formula-XXXIII starting material with 16-(3-chlorophenoxy)-17,18,19,20-tetranor-cis-4,5-didehydro-PGF$_1$α, methyl ester (Netherlands Pat. No. 7703950, Derwent Farmdoc Abstract 80703Y), a mixture of the title compounds is obtained. They are separated by high pressure liquid chromatography as the less polar (5R) and more polar (5S) title compounds.

EXAMPLE 37

(5R)- and
(5S)-9-Deoxy-5,9α-epoxy-16-(3-chlorophenoxy)-13,14-dihydro-17,18,19,20-tetranor-PGF$_1$, Methyl Ester Following the procedures of Example 26 the compounds of Example 36, namely (5R)- and (5S)-9-deoxy-5,9α-epoxy-16-(3-chlorophenoxy)-17,18,19,20-tetranor-PGF$_1$, methyl ester are hydrogenated at atmospheric pressure in methanol in the presence of catalytic amounts of palladium (10%)-on-carbon and sodium nitrite. The title compounds are separated by HPLC as the less polar (5R) and more polar (5S) compounds.

EXAMPLE 38

(2E,5R) and
(2E,5S)-9-Deoxy-5,9α-epoxy-2,3-didehydro-16-(3-chlorophenoxy)-17,18,19,20-tetranor-PGF$_1$, Methyl Ester I. Following the procedures of Example 22, the (5R)-9-deoxy-5,9α-epoxy-16-(3-chlorophenoxy)-17,18,19,20-tetranor-PGF$_1$, methyl ester of Example 36 is blocked at C-11 and C-15 with t-butyldimethylsilyl groups. The 2-phenylselenide is then prepared.

II. Following the procedures of Example 23, the phenylselenide above is treated with aqueous hydrogen peroxide to prepare the 2,3-didehydro compound.

III. Following the procedures of Example 24 the silyl groups are replaced by hydrolysis and the (2E,5R) title compound obtained.

Likewise following the above steps but starting instead with the corresponding (5S) compound of Example 36, the (2E,5S) title compound is obtained.

EXAMPLE 39

(2E,5R)- and
(2E,5S)-9-Deoxy-5,9α-epoxy-2,3-didehydro-16-(3-chlorophenoxy)-13,14-dihydro-17,18,19,20-tetranor-PGF$_1$, Methyl Ester Following the procedures of Example 38 parts I–III, but replacing the starting material with the (5R)- and (5S)-9-deoxy-5,9α-epoxy-16-(3-chlorophenoxy)-13,14-dihydro-17,18,19,20-tetranor-PGF$_1$, methyl ester compounds of Example 37, the above title compounds are obtained.

Following the procedures of Examples 2–39 but employing the appropriate starting materials available by methods described herein or known in the art, there are obtained the following 9-deoxy-5,9α-epoxy-PGF$_1$-type compounds within the scope of formula III, as the respective less polar isomer and more polar isomer of each pair of C-5 isomers:

9-deoxy-5ξ,9α-epoxy-16,16-dimethyl-PGF$_1$, methyl ester
9-deoxy-5ξ,9α-epoxy-16,16-difluoro-PGF$_1$, methyl ester
9-deoxy-5ξ,9α-epoxy-17-phenyl-18,19,20-trinor-PGF$_1$, methyl ester
9-deoxy-5,9α-epoxy-16,16-dimethyl-16-(3-chlorophenoxy)-17,18,19,20-tetranor-PGF$_1$, methyl ester
9-deoxy-5,9α-epoxy-16-[(3-trifluoromethyl)phenoxy]-17,18,19,20-tetranor-PGF$_1$, methyl ester
9-deoxy-5ξ,9α-epoxy-13,14-dihydro-16,16-dimethyl-PGF$_1$, methyl ester
9-deoxy-5ξ,9α-epoxy-13,14-dihydro-16,16-difluoro-PGF$_1$, methyl ester
9-deoxy-5ξ,9α-epoxy-13,14-dihydro-16-phenoxy-17,18,19,20-tetranor-PGF$_1$, methyl ester
9-deoxy-5ξ,9α-epoxy-13,14-dihydro-17-phenyl-18,19,20-trinor-PGF$_1$, methyl ester
9,15-dideoxy-5ξ,9α-epoxy-PGF$_1$, methyl ester
9,11-dideoxy-5ξ,9α-epoxy-11-oxo-PGF$_1$, methyl ester
9,11-dideoxy-5ξ,9α-epoxy-13,14-dihydro-11-oxo-PGF$_1$, methyl ester
(2E)-2,3-didehydro-9,11-dideoxy-5ξ,9α-epoxy-11-oxo-PGF$_1$, methyl ester
(2E)-2,3-didehydro-9,11-dideoxy-5ξ,9α-epoxy-13,14-dihydro-11-oxo-PGF$_1$, methyl ester
9,11-dideoxy-5ξ,9α-epoxy-11-oxo-(15S)-15-methyl-PGF$_1$, methyl ester
(2E)-2,3-didehydro-9-deoxy-5ξ,9α-epoxy-(15S)-15-methyl-PGF$_1$, methyl ester
(2E)-2,3-didehydro-9-deoxy-5ξ,9α-epoxy-16,16-dimethyl-PGF$_1$, methyl ester
(2E)-2,3-didehydro-9-deoxy-5ξ,9α-epoxy-16,16-difluoro-PGF$_1$, methyl ester
(2E)-2,3-didehydro-9-deoxy-5ξ,9α-epoxy-16-phenoxy-17,18,19,20-tetranor-PGF$_1$, methyl ester
(2E)-2,3-didehydro-9-deoxy-5ξ,9α-epoxy-17-phenyl-18,19,20-trinor-PGF$_1$, methyl ester
(2E)-2,3-didehydro-9,15-dideoxy-5ξ,9α-epoxy-PGF$_1$, methyl ester
(2E)-2,3-didehydro-9,15-dideoxy-5ξ,9α-epoxy-113,14-dihydro-PGF$_1$, methyl ester
(2E)-2,3-didehydro-9-deoxy-5ξ,9α-epoxy-13,14-dihydro-16,16-dimethyl-PGF$_1$, methyl ester
(2E)-2,3-didehydro-9-deoxy-5ξ,9α-epoxy-13,14-dihydro-16,16-difluoro-PGF$_1$, methyl ester
(2E)-2,3-didehydro-9-deoxy-5ξ,9α-epoxy-13,14-dihydro-16-phenoxy-17,18,19,20-tetranor-PGF$_1$, methyl ester
(2E)-2,3-didehydro-9-deoxy-5ξ,9α-epoxy-13,14-dihydro-17-phenyl-18,19,20-trinor-PGF$_1$, methyl ester Likewise following the procedures herein, there are obtained the free acids, amides, and N-methanesulfonylamides corresponding to each of the above named methyl esters, in each of their C-5 isomeric configurations.

Likewise following the procedures herein, there are obtained the amides and N-methanesulfonylamides of each of the following compounds, in each of their C-5 isomeric configurations:

9-deoxy-5ξ,9α-epoxy-PGF$_1$
9-deoxy-5ξ,9α-epoxy-(15S)-15-methyl-PGF$_1$
9-deoxy-5ξ,9α-epoxy-(15R)-15-methyl-PGF$_1$
9-deoxy-5ξ,9α-epoxy-16-phenoxy-17,18,19,20-tetranor-PGF$_1$
9-deoxy-5ξ,9α-epoxy-13,14-dihydro-PGF$_1$
9,15-dideoxy-5ξ,9α-epoxy-13,14-dihydro-PGF$_1$ (2E)-2,3-didehydro-9-deoxy-5ξ,9α-epoxy-PGF₁
(2E)-2,3-didehydro-9-deoxy-5ξ,9α-epoxy-13,14-dihydro-PGF₁.

I claim:

1. A cyclic ether of the formula

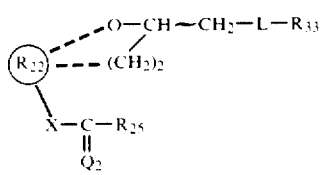

wherein L is (1) —(CH₂)$_d$— wherein D is one to 5, inclusive, (2) —(CH₂)$_t$—CF₂— wherein t is one, 2, or 3, (3) —CH=CH—, or (4) —CH₂—O—CH₂—Y— wherein Y is a valence bond or —(CH₂)$_k$— wherein k is one or 2; wherein Q₂ is

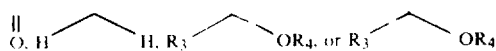

wherein R₃ is hydrogen or alkyl of one to 4 carbon atoms, inclusive, and wherein R₄ is hydrogen; wherein (R₂₂) is

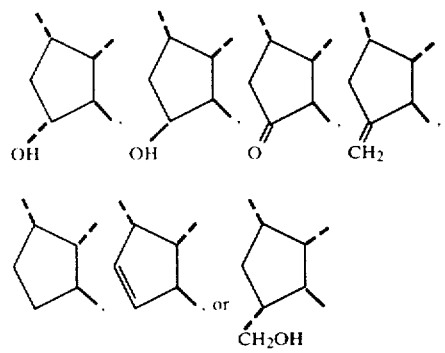

wherein R₂₅ is

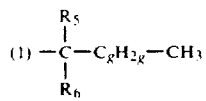

wherein C$_g$H$_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro; or

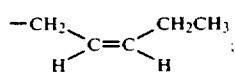

wherein R₃₃ is

 (1)

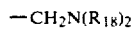 (2)

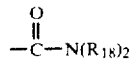 (3)

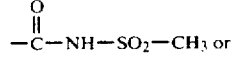 (4)

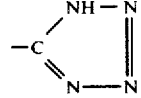 (5)

wherein R₁₈ is hydrogen, alkyl of one to 12 carbon atoms, inclusive, benzyl, or phenyl, being the same or different, wherein X is cis- or trans-CH=CH—, —C≡C—, or —CH₂CH₂—; and wherein ~ indicates attachment in alpha or beta configuration; including the lower alkanoates thereof.

2. A compound according to claim 1, wherein X is trans-CH=CH—.

3. A compound according to claim 2, wherein Q₂ is

wherein R₃ and R₄ are defined as in claim 1.

4. A compound according to claim 3, wherein (R₂₂) is

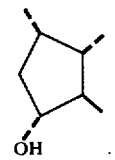

5. A compound according to claim 4, wherein L is —(CH₂)$_d$— wherein d is one to 5 inclusive 6. A compound according to claim 5, wherein R₂₅ is

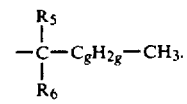

7. A compound according to claim 6, wherein

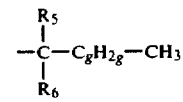

is n-pentyl.

8. A compound according to claim 7, wherein R₃ and R₄ are hydrogen.

9. A compound according to claim 8, wherein R₃₃ is —CH₂OH.

10. (5R)-2-Decarboxy-9-deoxy-5,9α-epoxy-2-hydroxymethyl-PGF₁, a compound according to claim 9.

11. (5S)-2-Decarboxy-9-deoxy-5,9α-epoxy-2-hydroxymethyl-PGF₁, a compound according to claim 9.

12. A compound according to claim 8, wherein $R_{33}$ is $$-\overset{O}{\underset{\|}{C}}-N(R_{18})_2$$

wherein $R_{18}$ is defined as in claim 1.

13. (5R)-9-Deoxy-5,9α-epoxy-PGF$_1$, amide, a compound according to claim 12.

14. (5S)-9-Deoxy-5,9α-epoxy-PGF$_1$, amide, a compound according to claim 12.

15. A compound according to claim 8, wherein $R_{33}$ is $$-\overset{O}{\underset{\|}{C}}-NH-SO_2-CH_3.$$

16. (5R)-9-Deoxy-5,9α-epoxy-PGF$_1$, N-methanesulfonylamide, a compound according to claim 15.

17. (5S)-9-Deoxy-5,9α-epoxy-PGF$_1$, N-methanesulfonylamide, a compound according to claim 15.

18. A compound according to claim 7, wherein $R_3$ is methyl and $R_4$ is hydrogen.

19. A compound according to claim 18, wherein $R_{33}$ is —CH$_2$OH.

20. (5R,15S)-2-Decarboxy-9-deoxy-5,9α-epoxy-2-hydroxymethyl-15-methyl-PGF$_1$, a compound according to claim 19.

21. (5S,15S)-2-Decarboxy-9-deoxy-5,9α-epoxy-2-hydroxymethyl-15-methyl-PGF$_1$, a compound according to claim 19.

22. A compound according to claim 18, wherein $R_{33}$ is $$-\overset{O}{\underset{\|}{C}}-NH-SO_2-CH_3.$$

23. (5R,15S)-9-Deoxy-5,9α-epoxy-15-methyl-PGF$_1$, N-methanesulfonylamide, a compound according to claim 22.

24. (5S,15S)-9-Deoxy-5,9α-epoxy-15-methyl-PGF$_1$, N-methanesulfonylamide, a compound according to claim 22.

25. A compound according to claim 4, wherein L is —CH=CH—.

26. A compound according to claim 25, wherein $R_{25}$ is $$-\underset{\underset{R_6}{|}}{\overset{\overset{R_5}{|}}{C}}-C_gH_{2g}-CH_3.$$

27. A compound according to claim 26, wherein $$-\underset{\underset{R_6}{|}}{\overset{\overset{R_5}{|}}{C}}-C_gH_{2g}-CH_3$$

is n-pentyl.

28. A compound according to claim 27, wherein $R_{33}$ is —CH$_2$OH.

29. (2E,5R)-2-Decarboxy-2,3-didehydro-9-deoxy-5,9α-epoxy-2-hydroxymethyl-PGF$_1$, a compound according to claim 28.

30. (2E,5S)-2-Decarboxy-2,3-didehydro-9-deoxy-5,9α-epoxy-2-hydroxymethyl-PGF$_1$, a compound according to claim 28.

31. A compound according to claim 27, wherein $R_{33}$ is $$-\overset{O}{\underset{\|}{C}}-N(R_{18})_2$$

wherein $R_{18}$ is defined as in claim 1.

32. (2E,5R)-2,3-Didehydro-9-deoxy-5,9α-epoxy-PGF$_1$, amide, a compound according to claim 31.

33. (2E,5S)-2,3-Didehydro-9-deoxy-5,9α-epoxy-PGF$_1$, amide, a compound according to claim 31.

34. A compound according to claim 27, wherein $R_{33}$ is $$-\overset{O}{\underset{\|}{C}}-NH-SO_2-CH_3.$$

35. (2E,5R)-2,3-Didehydro-9-deoxy-5,9α-epoxy-PGF$_1$, N-methanesulfonylamide, a compound according to claim 34.

36. (2E,5S)-2,3-Didehydro-9-deoxy-5,9α-epoxy-PGF$_1$, N-methanesulfonylamide, a compound according to claim 34.

37. A compound according to claim 27, wherein $R_{33}$ is $$-C\begin{matrix}\diagup NH-N\\ \diagdown \| \\ N\!-\!-\!N\end{matrix}$$

38. (2E,5R)-2-Decarboxy-2,3-didehydro-9-deoxy-5,9α-epoxy-2-(1H-tetrazol-5-yl)-PGF$_1$, a compound according to claim 36.

39. (2E,5S)-2-Decarboxy-2,3-didehydro-9-deoxy-5,9α-epoxy-2-(1H-tetrazol-5-yl)-PGF$_1$, a compound according to claim 36.

40. A compound according to claim 2, wherein $Q_2$ is $$R_3\diagup\!\!\diagdown OR_4$$

wherein $R_3$ and $R_4$ are defined as in claim 1.

41. A compound according to claim 40, wherein $R_{22}$ is

42. A compound according to claim 41, wherein L is —(CH$_2$)$_d$— wherein d is one to 5 inclusive.

43. A compound according to claim 42, wherein d is 2.

44. A compound according to claim 43, wherein $R_{25}$ is

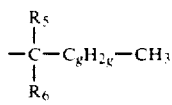

45. A compound according to claim 44, wherein

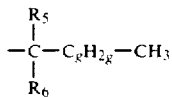

is n-pentyl.

46. A compound according to claim 45, wherein $R_3$ is methyl and $R_4$ is hydrogen.

47. A compound according to claim 46, wherein $R_{33}$ is

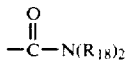

wherein $R_{18}$ is defined as in claim 1.

48. (5R,15R)-9-Deoxy-5,9α-epoxy-15-methyl-PGF$_1$, amide, a compound according to claim 47.

49. (5S,15R)-9-Deoxy-5,9α-epoxy-15-methyl-PGF$_1$, amide, a compound

50. A compound according to claim 46, wherein $R_{33}$ is $$-\overset{O}{\underset{\|}{C}}-NH-SO_2-CH_3.$$

according to claim 47.

51. (5R,15R)-9-Deoxy-5,9α-epoxy-15-methyl-PGF$_1$, N-methanesulfonylamide, a compound according to claim 50.

52. (5S,15R)-9-Deoxy-5,9α-epoxy-15-methyl-PGF$_1$, N-methanesulfonylamide, a compound according to claim 50.

53. A compound according to claim 1, wherein X is —CH$_2$CH$_2$—.

54. A compound according to claim 53, wherein $Q_2$ is

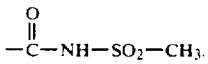

wherein $R_3$ and $R_4$ are defined as in claim 1.

55. A compound according to claim 54, wherein L is —(CH$_2$)$_d$— wherein d is one to 5, inclusive.

56. A compound according to claim 55, wherein $R_{33}$ is —CH$_2$OH.

57. (5R)-2-Decarboxy-9-deoxy-5,9α-epoxy-13,14-dihydro-2-hydroxymethyl-PGF$_1$, a compound according to claim 56.

58. (5E)-2-Decarboxy-9-deoxy-5,9α-epoxy-13,14-dihydro-2-hydroxymethyl-PGF$_1$, a compound according to claim 56.

59. A compound according to claim 55, wherein $R_{33}$ is

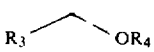

wherein $R_{18}$ is defined as in claim 1.

60. (5R)-9-Deoxy-5,9α-epoxy-13,14-dihydro-PGF$_1$, amide, a compound according to claim 59.

61. (5S)-9-Deoxy-5,9α-epoxy-13,14-dihydro-PGF$_1$, amide, a compound according to claim 59.

62. A compound according to claim 54, wherein L is —CH=CH—.

63. A compound according to claim 62, wherein $R_{33}$ is —CH$_2$OH.

64. (2E,5R)-2-Decarboxy-2,3-didehydro-9-deoxy-5,9α-epoxy-13,14-dihydro-2-hydroxymethyl-PGF$_1$, a compound according to claim 63.

65. (2E,5S)-2-Decarboxy-2,3-didehydro-9-deoxy-5,9α-epoxy-13,14-dihydro-2-hydroxymethyl-PGF$_1$, a compound according to claim 63.

66. A compound according to claim 62 wherein $R_{33}$ is $$-\overset{O}{\underset{\|}{C}}-NH-SO_2-CH_3.$$

67. (2E,5R)-2,3-Didehydro-9-deoxy-5,9α-epoxy-13,14-dihydro-PGF$_1$, N-methanesulfonylamide, a compound according to claim 66.

68. (2E,5S)-2,3-Didehydro-9-deoxy-5,9α-epoxy-13,14-dihydro-PGF$_1$, N-methanesulfonylamide, a compound according to claim 66.

69. A compound according to claim 53, wherein $Q_2$ is

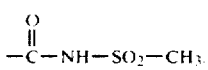

70. A compound according to claim 69, wherein $R_{33}$ is

wherein $R_{18}$ is defined as in claim 1.

71. (5R)-9,15-Dideoxy-5,9α-epoxy-13,14-dihydro-PGF$_1$, amide, a compound according to claim 70.

72. (5S)-9,15-Dideoxy-5,9α-epoxy-13,14-dihydro-PGF$_1$, amide, a compound according to claim 70.

73. A compound according to claim 69, wherein $R_{33}$ is

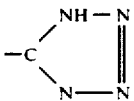

74. (5R)-2-Decarboxy-9,15-dideoxy-5,9α-epoxy-13,14-dihydro-2-(1H-tetrazol-5-yl)-PGF$_1$, a compound according to claim 73.

75. (5S)-Decarboxy-9,15-dideoxy-5,9α-epoxy-13,14-dihydro-2-(1H-tetrazol-5-yl)-PGF$_1$, a compound according to claim 73.

76. A cyclic ether of the formula

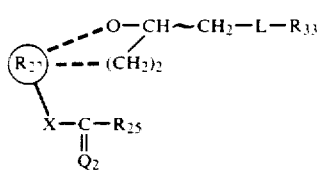

wherein L is (1) —(CH$_2$)$_d$—, wherein d is one to 5, inclusive, (2) —(CH$_2$)$_t$—CF$_2$—, wherein t is one, 2, or 3, (3) —CH=CH—, or (4) —CH$_2$—O—CH$_2$—Y—, wherein Y is a valence bond or —(CH$_2$)$_k$—, wherein k is one or 2; wherein Q$_2$ is

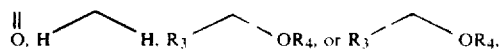

wherein R$_3$ is hydrogen or alkyl of one to 4 carbon atoms, inclusive, and wherein R$_4$ is hydrogen; wherein R$_{22}$ is

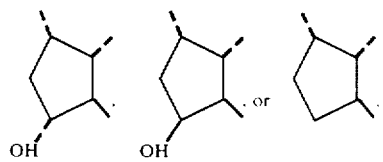

wherein R$_{25}$ is

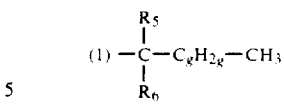

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro; or

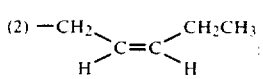

wherein R$_{33}$ is (1) —CH$_2$OH,

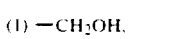

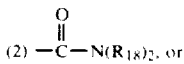

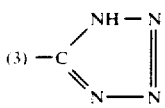

wherein R$_{18}$ is hydrogen, alkyl of one to 12 carbon atoms, inclusive, benzyl, or phenyl being the same or different, wherein X is cis- or trans-CH=CH—, or —C≡C—, or —CH$_2$CH$_2$—; and wherein ~ indicates attachment in alpha or beta configuration; including the lower alkanoates thereof.

* * * * *

UNITED STATES PATENT OFFICE
CERTIFICATE OF CORRECTION

Patent No. 4,490,538  Dated 25 December 1984

Inventor(s) Roy A. Johnson

It is certified that error appears in the above-identified patent and that said Letters Patent are hereby corrected as shown below:

Column 2, line 20, "ctiology is " should be -- etiology is --.
Column 2, line 36, "of while blood" should be -- of whole blood --.
Column 4, line 62, "as eethanol," should read -- as ethanol,--.
Column 8, lines 35-36, "wherein $R_{12}$ is the same as $R_{12}$ is the same as $R_4$"

should read -- wherein $R_{12}$ is the same as $R_4$ --.
Column 11, line 67, "$R_{14}R_{15}$ are" should read -- $R_{14}$ and $R_{15}$ are --.

Column 12, lines 12-18, last formula should read as follows:

or 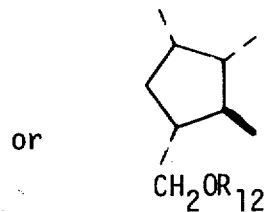

Column 14, line 4, "to 12 1 carbon " should read -- to 12 carbon --.
Column 16, line 12, "of one 4 carbon atoms" should read -- of one to 4 carbon atoms --.
Column 21, line 49, "of formula II" should read -- of formula III --.
Column 23, line 29, "XXIV" should read -- XXXIV --.
Column 23, line 31, part of XXXIV "$CH_2-L-R_1$" should read -- $CH-L-R_1$ --.
Column 24, line 2, "preference in" should read -- preference is --.
Column 24, line 11, "formula VIII is" should read -- formula VII is --.
Column 25, line 18, "or -P(O)(OR$_{20}$)$_2$" should read -- or -p(O)(R$_{20}$)$_2$ --.

Column 46, line 39, "of the il in" should read -- of the oil in --.
Column 46, line 50, "349, 323, 199," should read -- 349, 323, 321, 199, --.
Column 47, line 9, "-Phenylphenacy" should read -- -Phenylphenacyl --.
Column 48, line 2, "and 1.40" should read -- and 14.0 --.
Column 49, line 49, "imidazole (0.026 g)" should read -- imidazole (0.206 g) --.

UNITED STATES PATENT OFFICE
CERTIFICATE OF CORRECTION

Patent No. 4,490,538            Dated     25 December 1984

Inventor(s)    Roy A. Johnson

It is certified that error appears in the above-identified patent and that said Letters Patent are hereby corrected as shown below:

Column 51, line 20, "5.14.3491, 443," should read -- 514.3491, 443, --.
Column 56, line 41, "epoxy-113,14-" should read -- epoxy-13,14- --.
Column 60, claim 37, part of form should appear as follows:

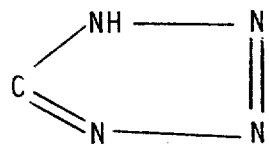

Column 61, claim 49, line 32, "compound" should read -- compound according to claim 47. --.
Column 61, claim 50, line 39, "according to claim 47" should be deleted.
Column 62, claim 73, part of form should appear as follows:

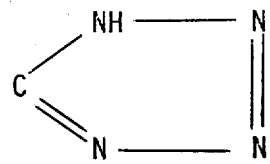

Signed and Sealed this

First Day of July 1986

[SEAL]

Attest:

DONALD J. QUIGG

Attesting Officer    Commissioner of Patents and Trademarks